United States Patent [19]
Simon et al.

[11] Patent Number: 5,851,789
[45] Date of Patent: Dec. 22, 1998

[54] METHODS AND AGENTS FOR MEASURING AND CONTROLLING MULTIDRUG RESISTANCE

[75] Inventors: Sanford M. Simon, New York, N.Y.; Melvin M. S. Schindler, Okemos, Mich.

[73] Assignees: The Rockefeller University, New York, N.Y.; Board of Trustees Operating Michigan State University, East Lansing, Mich.

[21] Appl. No.: 535,995

[22] Filed: Sep. 29, 1995

Related U.S. Application Data

[63] Continuation of Ser. No. 379,875, Jan. 27, 1995, abandoned, which is a continuation of Ser. No. 190,336, Feb. 1, 1994, abandoned.

[51] Int. Cl.$^6$ .............................. C12Q 1/18; C12Q 1/02; G01N 21/80; G01N 31/00
[52] U.S. Cl. ................. 435/32; 424/7.1; 435/2; 435/4; 435/29; 436/163; 436/172
[58] Field of Search ................. 424/7.1; 435/2, 435/4, 29, 32; 436/163, 172

[56] References Cited

U.S. PATENT DOCUMENTS

| | | | |
|---|---|---|---|
| 4,208,414 | 6/1980 | Schinitsky | 514/283 |
| 4,336,334 | 6/1982 | Powell et al. | 435/146 |
| 5,005,588 | 4/1991 | Rubin | 607/2 |
| 5,135,859 | 8/1992 | Witholt et al. | 435/135 |
| 5,302,525 | 4/1994 | Groleau et al. | 435/252.1 |
| 5,369,009 | 11/1994 | Arceci et al. | 424/1.49 |

FOREIGN PATENT DOCUMENTS

| | | |
|---|---|---|
| 0568126 | 11/1993 | European Pat. Off. . |
| WO 95/21381 | 8/1995 | WIPO . |

OTHER PUBLICATIONS

Schindler et al. (1996) Biochemistry 35:2811–7.
Simon et al. (1994) Proc. Natl. Acad. Sci. USA 91:1128–32.
Altenberg et al. (1993) Proc. Natl. Acad. Sci USA 90:9735–8.
Altenberg et al. (1993) Fed. Am. Soc. Exp. Biol. (FASEB) J. 7:A810.
Hamilton et al. (1993) Anticancer Res. 13:2059–64.
Roepe et al. (1993) Biochemistry 32:11042–56.
Science News (1993) "Take home message: No AIDS magic bullet" (Oct. 2).
Roepe et al. (1992) J. Gen. Physiol. 100(6):52A.
Roepe P.D. (1992) Biochemistry 31:12555–64.
Versantvoort et al. (1992) Intl. J. Cancer 50:906–11.
Thiebaut et al., 1990, J. Histochem. Cytochem. 38:685–90.
Boscoboinik et al. (1990) Br. J. Cancer 61(4):568–72.
Keizer and Joenje, 1989, J. Natl. Cancer Inst. 81:706–9.
Warburg, O. (1956) Science 123:309–14.
Di Marco et al., 1977, Chem. Biol. Interact. 19:291–302.
Owellen et al., 1977, Biochem. Pharm. 26:1213–19.
Skovsgaard, 1977, Biochem. Pharm. 26:215–22.
Boron, 1986, Annu. Rev. Physiol. 48:377–88.
Epand et al., 1991, Br. J. Cancer 63:247–51.

*Primary Examiner*—Nancy Degen
*Attorney, Agent, or Firm*—Klauber & Jackson

[57] ABSTRACT

The predominant effect of pH change on multidrug resistance (MDR) independent of active drug efflux has been demonstrated in tumor cells through studies of the drugs doxorubicin and daunomycin. Specifically, the distribution of both drugs was monitored in fibroblasts and myeloma cells to examine the role of pH in drug partitioning. The invention comprises in one aspect the treatment of MDR by administering a therapeutically effective amount of a pH modulator. Diagnostic utilities are contemplated and extend to drug discovery assays and methods for measuring monitoring the status of the onset or development of pH-related conditions such as MDR, as well as the measurement of intracellular drug accumulation. Therapeutic compositions include a composition comprising a pH modulator alone or in combination with the dose-limited therapeutic agent(s), and a pharmaceutically acceptable excipient, are also contemplated.

21 Claims, 13 Drawing Sheets

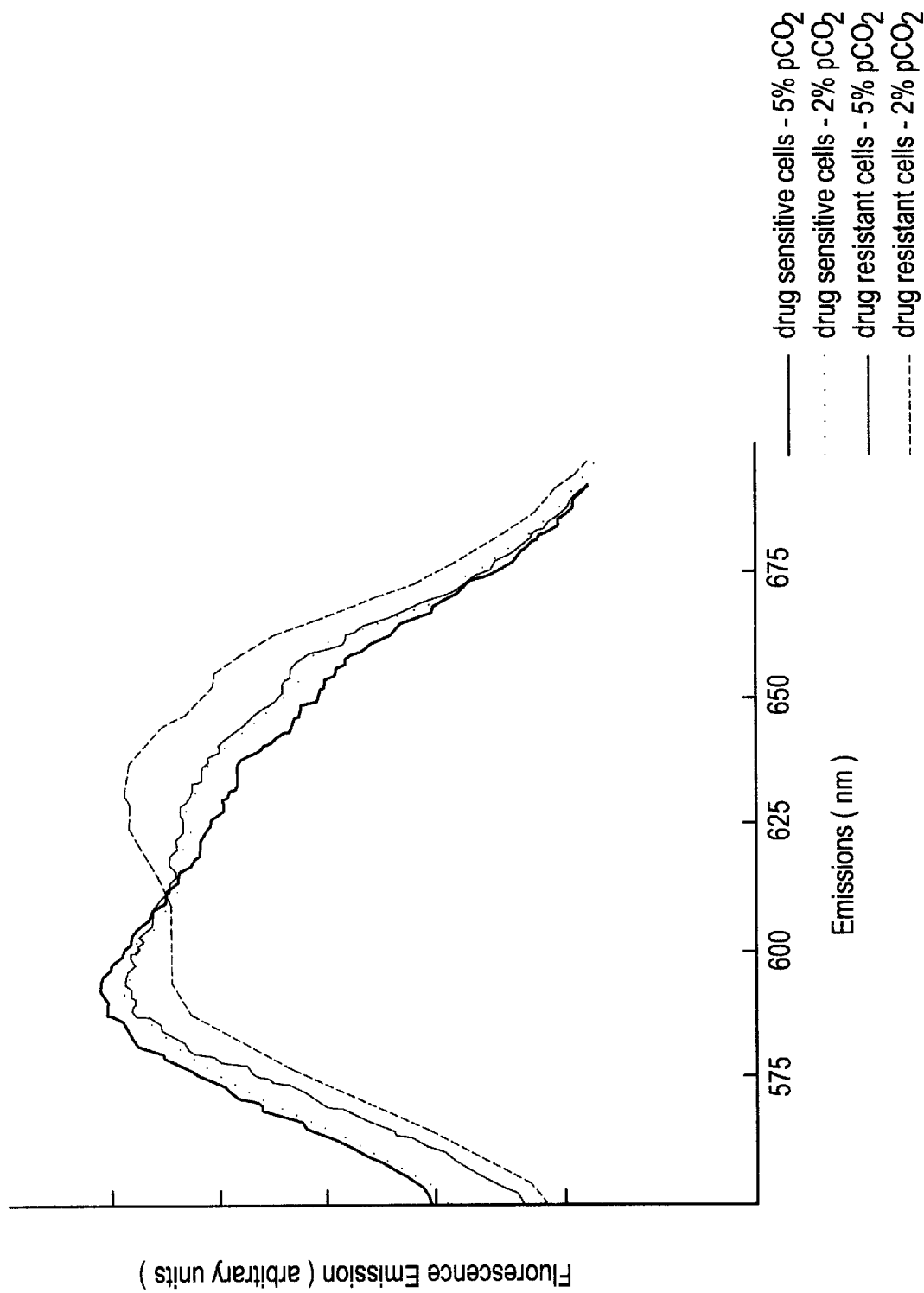

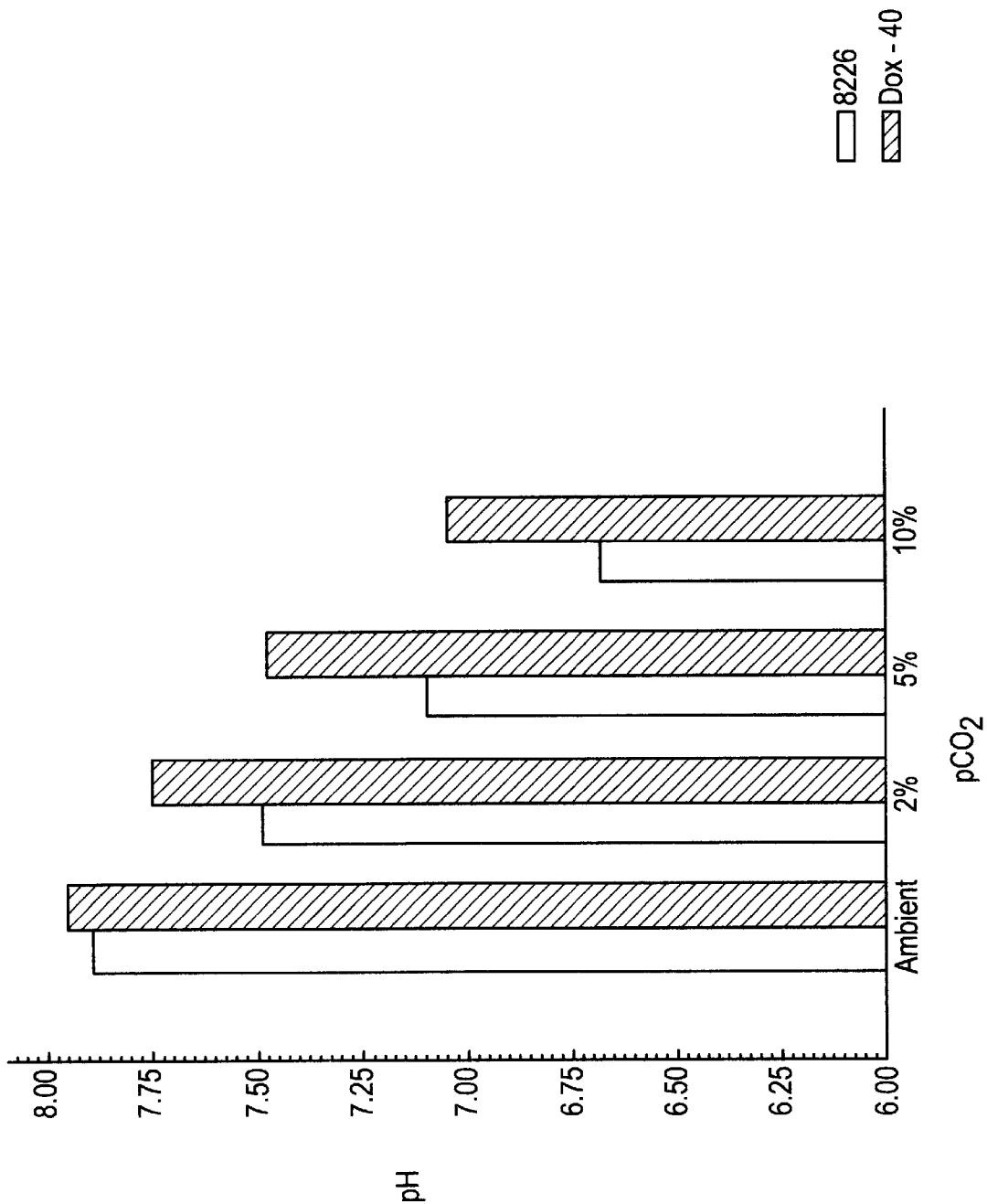

5% CO$_2$　　　2% CO$_2$　　　5% CO$_2$　　　2% CO$_2$

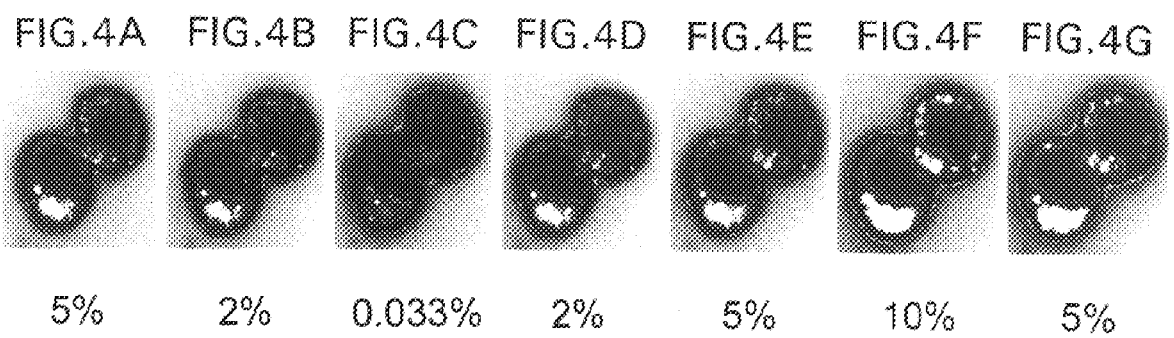

FIG.5A  MCF-7

FIG.5B  MCF-7adr control nigericin acridine orange

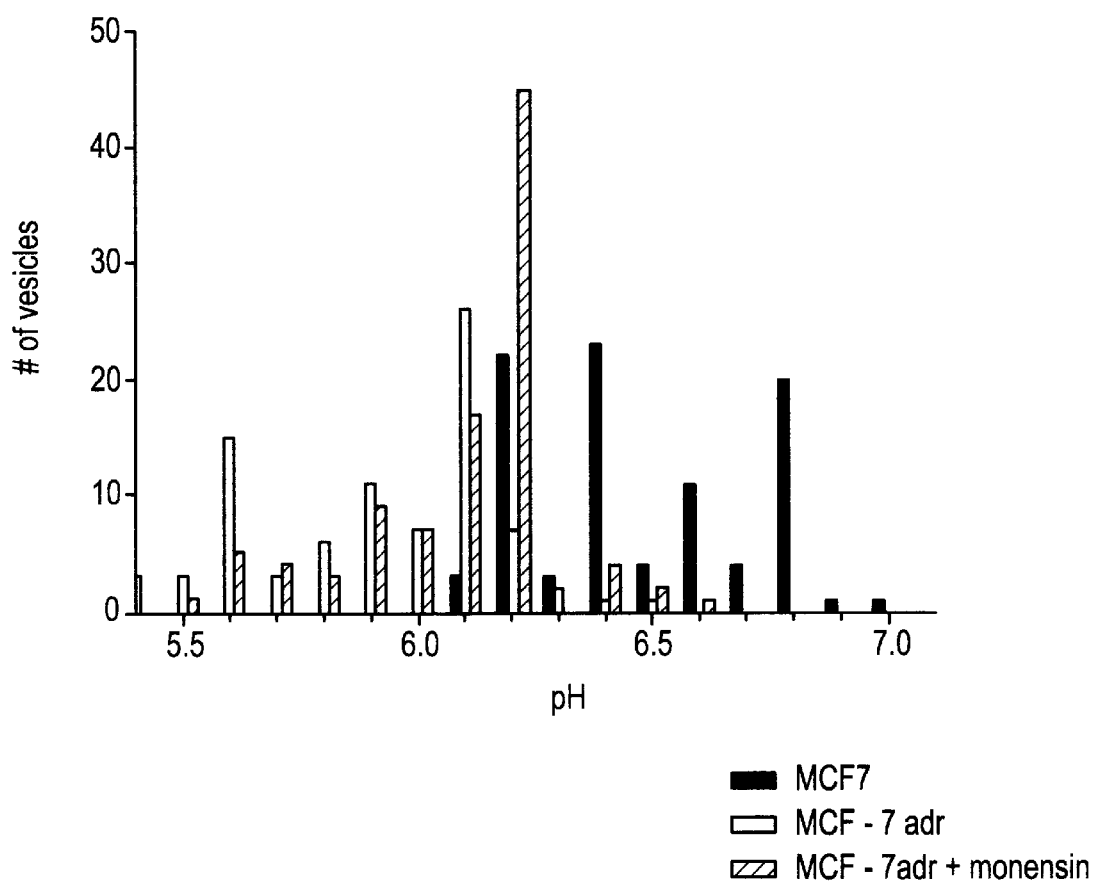

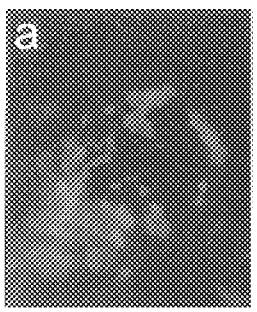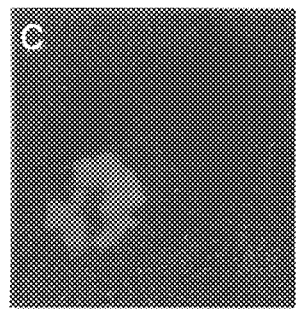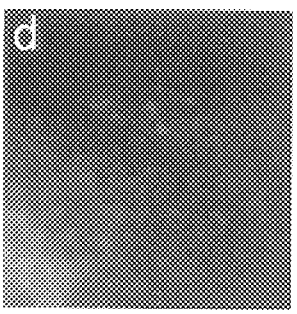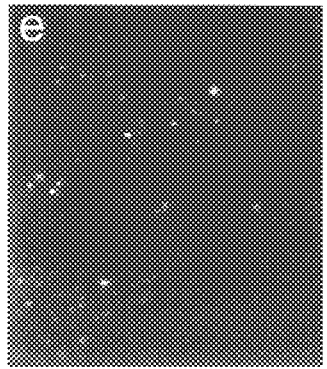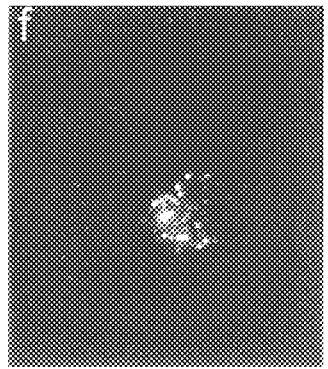

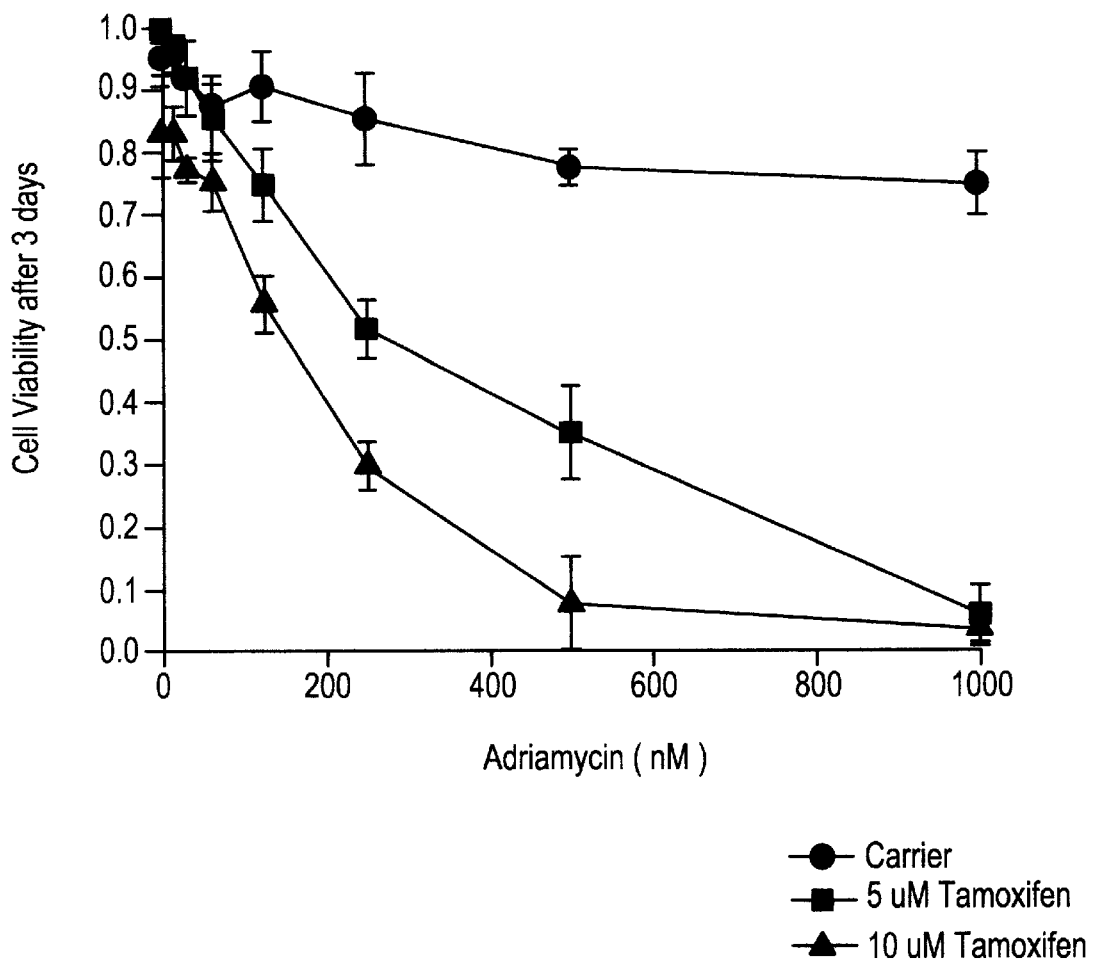

METHODS AND AGENTS FOR MEASURING AND CONTROLLING MULTIDRUG RESISTANCE

CROSS-REFERENCE TO RELATED APPLICATIONS

This application is a continuation-in-part of U.S. patent application Ser. No. 08/379,875, filed Jan. 27, 1995, now abandoned; which is a continuation of application Ser. No. 08/190,336, filed Feb. 1, 1994, now abandoned.

GOVERNMENT SUPPORT

The research leading to the present invention was funded in part by Grant No. GM 447005 from the National Institutes of Health. The government may have certain rights in the invention.

TECHNICAL FIELD OF THE INVENTION

The present invention relates generally to the field of immunology and, more particularly, to the condition known as multidrug resistance (MDR), and concerns the diagnosis and treatment of MDR and the discovery and development of effective pharmaceutical agents and therapies thereagainst.

BACKGROUND OF THE INVENTION

Chemotherapy takes advantage of the phenomena that tumor cells are ~5 fold more sensitive to anti-cancer drugs than are healthy cells. This narrow therapeutic window permits the use of cytotoxic agents to destroy malignancies. However, during chemotherapy, tumor cells often loose this sensitivity and become as vulnerable as normal cells. This diminished sensitivity to the original drug also extends to a broad class of other drugs, diverse in their structures and targets. This acquired multidrug resistance (MDR) is a major challenge to successful chemotherapy of malignant tumors.

Different drug-resistant cells overexpress a variety of membrane proteins including a subunit of a vacuolar H+-ATPase (1), a protein with homology to cystic fibrosis transmembrane conductance regulator (CFTR) (2) and the P-glycoprotein, a 170–180 kD plasma membrane glycoprotein (3). The most generally accepted hypothesis for MDR suggests the P-glycoprotein uses ATP to power a molecular pump that removes chemotherapeutic molecules from the cell (4)(and reviewed in (3)). This model proposes that chemotherapeutic agents diffuse down a concentration gradient into the cell and that the pump either transports the drugs out of the cytosol or serves as a flippase to expel them from the bilayer (5).

Over the past decade there have been a number of experiments that suggest that there might be changes of intracellular pH associated with multidrug resistance (MDR) in tumor cells. However, the preponderance of the thinking in this area maintains that a pump theory of drug expulsion predominates and that the change in pH is merely a secondary characteristic. It is toward the elucidation of this phenomenon and the proposal of diagnostic strategies coordinated therewith that the present invention is directed.

SUMMARY OF THE INVENTION

The present invention was born out of the discovery demonstrated herein that the shifts of pH that occur during multidrug resistance (MDR) are sufficient to produce the decreases in cellular drug accumulation observed in situ. In particular, the present invention demonstrates the following: (1) that the drug-sensitivity of tumor cells is the consequence of a defect in a component(s) of the exocytic apparatus; (2) that this defect is "normalized" in drug-resistant cells; (3) that any treatments that reverse MDR also disrupt the secretory pathway; and (4) that any manipulations that selectively disrupt and/or alkalinize exocytic compartments of MDR cells will reverse MDR.

Accordingly, the present invention contemplates methods for the discovery of drugs useful in the modulation of pH and the consequent control of MDR, and extends to the pharmaceutical compositions and corresponding therapeutic methods for their use.

The underlying investigations presented later on herein describe how these decreases can account for the effects of pH on all chemotherapeutic agents that are affected by MDR. The work also explains the observed mechanisms of MDR that are not dependent upon the expression of p-glycoprotein. Finally, assays are proposed and performed herein to select for drugs and treatments that will resensitize MDR cells to chemotherapeutic agents.

Accordingly, the invention extends in a first aspect to methods and corresponding kits for measuring pH accumulation in cells, and consequently measuring the onset or likelihood of occurrence of multidrug resistance. The methods also include the screening of drugs and other agents capable of modifying pH in vivo to counteract MDR to a degree sufficient to resensitize target cells such as neoplastic tumor cells, to effective treatment with chemotherapeutic agents. Particular methods include a scanning approach where for example, a pH sensitive dye such as SNARF1 is disposed within target cells and a variety of potential pH modifying drugs are introduced into separate samples, after which pH may be measured to determine efficacy of the particular drug under test. An alternate technique contemplates the characterization of the pH regulatory mechanism of a particular cell line under study, followed by the identification and administration of drugs that are able to modify the pH of these cell types, particularly to acidify MDR cells in preference to healthy cells of that cell type.

Therefore, in a further embodiment, the present invention contemplates administering, preferably intravenously, to a patient at risk or already experiencing multidrug resistance, a therapeutically effective amount of an agent capable of modifying intracellular pH, either alone or in combination or complex with the drug or drugs being administered pursuant to a preestablished therapeutic protocol. For example, cancer patients receiving doxorubicin or daunomycin who are about to or are experiencing MDR may be treated by the administration by intravenous, oral or other appropriate route, an effective amount of an agent capable of shifting cellular pH to the acidic range to facilitate the continued administration of the prescribed chemotherapeutic.

Further contemplated by the present invention are therapeutic compositions, typically in unit dose form, useful for preventing or ameliorating the onset of MDR or reversing or neutralizing its effect. The compositions comprise a pharmaceutically acceptable carrier containing one or more of a pH modulator of the present invention either alone or in combination with the previously prescribed chemotherapeutic agent as active ingredient(s).

A particular assay protocol may employ the pH indicator SNARF1. Accordingly, both normal and MDR cells would loaded with SNARF1, and aliquots would dispensed into separate tubes that are thereafter challenged with different potential pH modulating agents. Measurements of pH change would then be measured spectrofluorometrically. A further method contemplates the measurement of the effectiveness of a particular pH modulator by the measurement of the cellular concentration of a particular chemotherapeutic drug. Certain drugs such as daunomycin, are capable of spectrofluorimetric measurement.

Accordingly, it is a principal object of the present invention to provide a methods for preventing the development of multidrug resistance (MDR) in mammals.

It is a further object of the present invention to provide methods for the assessing the onset of MDR.

It is a further object of the present invention to provide a method and associated assay system for screening substances such as drugs, agents and the like, potentially effective in preventing or treating MDR in mammals.

It is a still further object of the present invention to provide pharmaceutical compositions for use in the prevention or treatment of MDR in mammals.

Other objects and advantages will become apparent to those skilled in the art from a review of the ensuing description which proceeds with reference to the following illustrative drawings.

BRIEF DESCRIPTION OF THE DRAWINGS

FIGS. 2A and 2B are graphs demonstrating the effect of $pCO_2$ on cytosolic pH: In FIG. 2A, myeloma cells were loaded with SNARF1 and the $pCO_2$ in the medium was shifted between 2% (dashed lines) and 5% (solid line). The fluorescence emission was recorded between 520 nm and 700 nm using an excitation of 514 nm for both the drug-sensitive (black line) or resistant cells (grey line). The pH (as indicated by the ratio of the emission at 630 nm to 585 nm) is indistinguishable between the sensitive cells in 2% $pCO_2$ (dashed black line) and the resistant cells in 5% $pCO_2$ (solid grey line). IN FIG. 2B, the pH is plotted for both the drug-sensitive cells (white) and resistant cells (grey) at 0.03%, 2%, 5% and 10% pCO2.

FIG. 4A–4G demonstrate the effect of shifting $pCO_2$ on the daunomycin fluorescence in myeloma cells. Myeloma cells attached to cover glass slips were incubated in 6 $\mu$M daunomycin for 40 min. and monitored under standard fluorescence microscopy. The $pCO_2$ perfusing the surface of the chamber was sequentially switched for 4 minute intervals from 5% to 2%, to 0.03%, to 2%, 5%, 10% and then returned to 5%. The cycle was repeated. The daunomycin concentration is pseudocolor coded with the lowest value in green and increasing levels in orange, red and yellow.

FIGS. 5A–5D Acridine orange staining of MCF-7 and MCF-7adr cells. Acridine orange, a label for the acidic compartments, labels (a) the drug-sensitive human breast cancer cells (MCF-7) labels weakly in contrast to (b) the labelling of the adriamycin resistant variant (MCF-7adr). Treatment of both cell lines with nigericin (7.5 $\mu$M) at room temperature resulted in the immediate loss of orange/red fluorescence within (c) MCF-7 and (d) MCF-7adr cells. It is interesting to note that although the pericentriolar region in MCF-7adr cells no longer stains red with acridine orange following treatment with nigericin, it remains visible as anunstained area with a green fluorescent background (1d). This suggests that it is the pH gradient between the pericentriolar compartment/vesicles and the cytoplasm that is altered not its integrity during the period of examination. Methods: Cells were seeded and grown in Dulbecco Modified Eagle's (DME) media containing 10% fetal calf serum (no phenol red) in Lab-Tek culture chambers (Nunc, Naperville, Ill.) maintained in an incubator at 37° C. and 5% $CO_2$. The media for the MCF-7adr cells was supplemented with adriamycin (0.5 $\mu$g/ml). Cells were utilized 3–4 days following plating. Acridine orange (2 $\mu$g/ml media; 4 mg/ml stock (in water) was added directly to the chambers and the cells were incubated with the dye at 37° C. for 30 minutes. Cells in the presence of acridine orange were then examined at room temperature with an Insight Bilateral Laser Scanning Confocal Microscope (Meridian Instruments, Okemos, Mich.). Excitation was at 488 nn (argon ion laser beam) and dual emission confocal images were sequentially recorded utilizing both a 530-30 band pass barrier filter (green fluorescence) and a 605 nm long pass barrier filter (red fluorescence). Acridine orange demonstrates a concentration dependent long wavelength shift in the fluorescence emission and shows a red fluorescence when accumulated to a high concentration within cellular compartments (acidic) and a green fluorescence when bound at lower concentration to membranes and/or nucleic acids. Optical sections of the fluorescent sample were recorded at 0.5 micron intervals. Typical individual sections are presented to demonstrate the distribution of acridine orange within the cytoplasmic and vesicular compartments. Human breast cancer cells (MCF-7) and the adriamycin resistant line (MCF-7adr) were obtained from Dr. William W. Wells of the Dept. of Biochemistry, Michigan State University.

FIGS. 6A–6C Measurements of Intravesicular pH utilizing SNAFL-calcein. (a) Gradients of intracellular pH are relatively absent from MCF7 cells as assayed by fluorescence of SNAFL-calcein. (b) In contrast, significantly pH gradients, including an acidic pericentriolar labelling is observed in MCF7adr cells. (c) The intravesicular pH in drug-resistant MCF-7adr cells (white bars) is more alkaline than the vesicular pH of the drug-sensitive parental MCF-7 (black bars). This acidic pH difference is reduced by treatment of MCF-7adr cells with monensin (dark grey). Methods: The acetoxymethylester derivative of SNAFL-calcein (15 $\mu$g/ml) (a ratiometeric fluorescent probe for pH) was added to both MCF-7 and MCF-7adr cells. The ester linked fluorescent probe enters the cell passively where the esters are hydrolyzed by esterases located in the cytoplasm and intracellular vesicles. The SNAFL-calcein is then ionically trapped within the cytoplasm and vesicular compartments. The cells were incubated at 37° C. for 45 minutes and then examined in with the Insight confocal fluorescence. Optical sections were obtained utilizing two different filter settings for emission (530-30 band pass barrier filter and 630 long pass filter) and a single excitation wavelength (488 nm) as previously described for carboxy SNARF-1. The pixel intensities obtained at the two different emission intensities were then divided to obtain a ratio image of the internalized pH probe. These images were then compared to standard curves that were obtained in the following manner. To obtain a quantitive relationship between emission ratios and pH, each SNAFL-calcein stained cell line was exposed to a buffer at a known pH containing nigericin/high $K^+$ (18 $\mu M$/150 mM KCl). This treatment equilibrates all the internal compartments of the cell to the pH buffer of the incubating buffer. By sequentially changing the pH buffer that is bathing the cells, a pH curve was generated for each cell line that demonstrated the relationship between the SNAFL-calcein fluorescence emission ratio and pH. These values were then incorporated into a pH imaging routine that provides a direct read-out of pH values for individual intracellular compartments that are queried on the computer screen. Differences in distribution and fluorescent intensity of SNAFL-calcein are observed following labeling of (a) MCF-7 and (b) MCF-7adr cells. (c) To prepare histograms of vesicular pH, 5 vesicles within a confocal section were analyzed/cell (20 cells per cell type). Cells treated with monensin were exposed to the drug (10 $\mu g$/ml of media) for 30 minutes at 37° C. prior to labeling with SNAFL-calcein as described above. All cells were examined at room temperature.

FIGS. 7A–7F Fluorescent labeling of the TGN and secretory vesicles with Bodipy-Ceramide. (a) The Golgi of MCF-7 cells is diffuse throughout the cytoplasm and, as observed in the enlargement (b), is in part vesicular and part cisternal, interconnected via fine tubules. (c) In contrast the Golgi of MCF-7adr cells is compact and pericentriolar and as observed in the enlargement, (d) small secretory vesicles are observed in the cytosol. (e) The diffuse distribution of endocytosed vesicles containing internalized bodipy lactalbumin in MCF-7 cells is different from the (e) compact pericentriolar localization observed in the drug-resistant MCF-7adr cells. Methods: Bodipy-ceramide (Bodipy-Cer; Molecular Probes, Eugene, Oreg.) has been demonstrated to label Golgi membranes[11]. Conversion of Bodipy-Cer to Bodipy-sphingomyelin (in cis golgi) results in the movement of this fluorescent lipid to the trans-Golgi network (TGN). As the Bodipy-sphingomyelin concentration increases within the TGN and secretory vesicles, a long wavelength shift in fluorescence occurs results in red fluorescent structures (TGN and secretory vesicles) against a green fluorescent background. Cells were incubated with Bodipy-Cer (3 $\mu g$/ml) for 15 minutes at 37° C., washed once with fresh media and then examined in optical section at room temperature with confocal fluorescence microscopy. Excitation was at 488 nm and dual emission images were prepared utilizing the filter set described for acridine orange (FIG. 1). To examine internalization, Bodipy-lactalbumin (Bodipy-Lac, Molecular Probes, Eurgene, OR) was used as a fluid phase marker. Cells were incubated with Bodipy-Lac (2 mg/ml) for 90 minutes at 37° and then washed once with cold media and rapidly examined with confocal fluorescence microscopy ($\lambda_{ex}$=488 nm, $\lambda_{em}$530-30 nm band pass filter). The images are as follows: (a) Bodipy-Cer labeling of MCF-7 cells, enlarged view of (b) showing tethered vesicles within MCF-cells (c) Bodipy-Cer labeling of MCF-7adr cells (d) Bodipy-Lac labeling of MCF-7 cells (e) and Bodipy-Lac labeling of MCF-7adr cells.

Distribution of adriamycin (top row)

Figure 1:
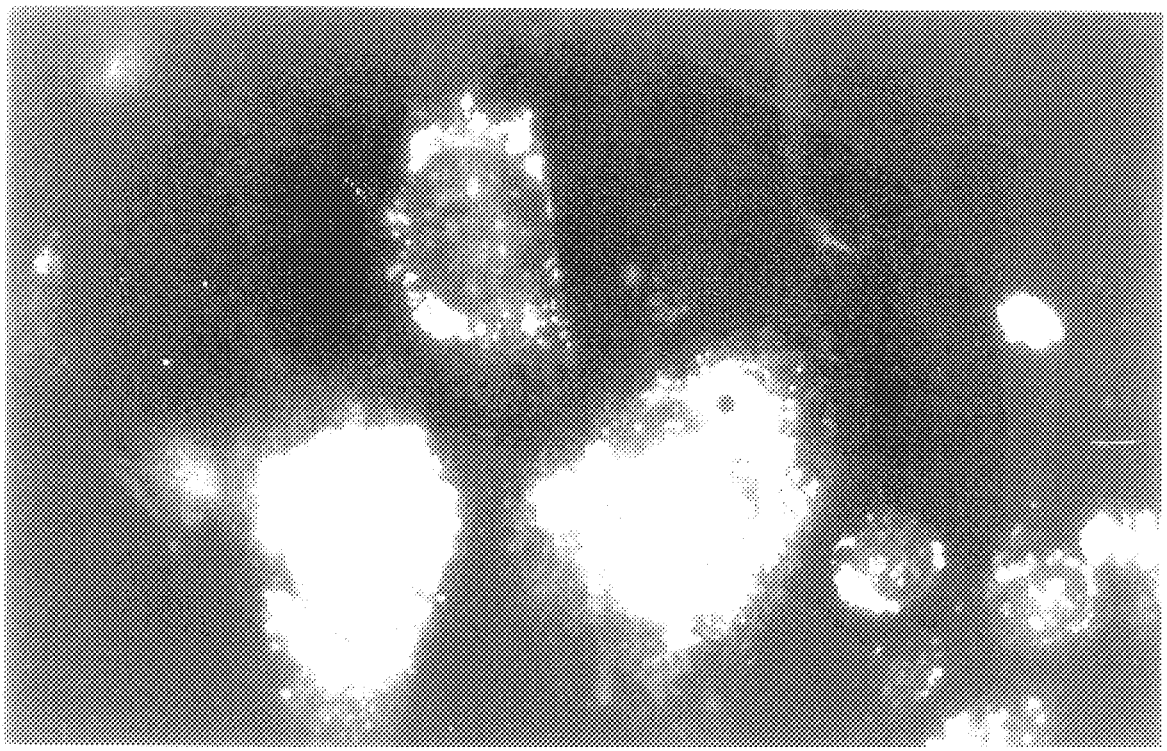
FIG. 1 is a fluorescence photomicrograph of the daunomycin fluorescence in NIH3T3 fibroblasts demonstrating the subcellular localization of daunomycin and doxorubicin. Daunomycin (5 $\mu$M) was added to the medium 45 min. prior to viewing with fluorescence microscopy.

Adriamycin (5 $\mu g$/ml) (Calbiochem, La Jolla, Calif.) distribution was examined following a 30 min. incubation with the drug at 37° C. in 5% CO2. in the absence or presence of tamoxifen (50 (M treatment for 20 min. at 37° C. and 5% CO2). Confocal fluorescence microscopy was performed with excitation at 488 nm (argon ion laser). MCF-7adr cells show a pericentriolar distribution of adriamycin (left) that changes to an intranuclear distribution following treatment with tamoxifen (50 (M) (Sigma, St. Louis, Mo.) (middle). This nuclear pattern of adriamycin labeling is similar to that observed within drug sensitive MCF-7 cells (right).

Acidic compartments (second row)

Acridine orange demonstrates a concentration dependent long wavelength shift in the fluorescence emission and shows a red fluorescence when accumulated to a high concentration within cellular compartments (acidic) and a green fluorescence when bound at lower concentration to membranes and/or nucleic acids. To examine intracellular acidic compartments, acridine orange (2 $\mu g$/ml media; 4 mg/ml stock (in water), Aldrich, Milwaukee, Wis.) was added directly to the chambers and the cells were incubated for 30 minutes. Cells in the presence of acridine orange were then examined utilizing an excitation at 488 nm and dual emission confocal images were sequentially recorded utilizing both a 530-30 band pass barrier filter (green fluorescence) and a 605 nm long pass barrier filter (red fluorescence). Optical sections of the fluorescent sample were recorded at 0.5 micron intervals. Typical individual sections are presented to demonstrate the distribution of acridine orange. MCF-7adr show a pericentriolar labeling (left) that disappears following treatment with tamoxifen (middle). Pericentriolar labeling is also absent in drug sensitive MCF-7 cells (right).

Trans-golgi network (third row)

Bodipy-ceramide (Bodipy-Cer; Molecular Probes, Eugene, OR) has been demonstrated to label Golgi compartments (11). Cells were incubated with Bodipy-Cer (3 $\mu g$/ml) for 15 minutes at 37° C., washed once with fresh media and then examined in optical sections. Excitation was at 488 nm and dual emission images were prepared utilizing the filter set described for acridine orange. A tight pericentriolar pattern of labeling is observed within MCF-7adr cells for Bodipy-Cer (left). This is disrupted following treatment with tamoxifen (middle) and is similar to that observed for the drug sensitive MCF-7 cells (right)

Endocytotic pathway (fourth row)

To examine internalization, Bodipy-lactalbumin (Bodipy-Lac, Molecular Probes, Eugene, Oreg.) was used as a fluid phase marker. Cells were incubated with Bodipy-Lac (2 mg/ml) for 90 minutes at 37° and then washed once with cold media and rapidly examined with confocal fluorescence microscopy ((ex =488 nm, (em 530-30 nm band pass filter). Excitation and emission wavelengths were as described for adriamycin. Bodipy-Lac is also observed to be concentrated within vesicles associated with a pericentriolar compartment in MCF-7adr cells (left). Bodipy-Lac staining following tamoxifen treatment is more punctate and diffuse within the cytoplasm with no localization to the pericentriolar region (middle) similar to its distribution in MCF-7 cells (right).

FIG. 9 shows adriamycin sensitivity studies in the absence and presence of tamoxifen. Cell viability assays were performed in the following manner: the media was removed 60 hr. after plating the cells and replaced with fresh media supplemented with various concentrations of adriamycin (Calbiochem, Calif.) and tamoxifen (solubilized in DMF 0.1%) (Sigma, St. Louis). After 6 h the media was removed, the cells rinsed, and then fed with fresh media not containing drugs. The cells were fed daily for three days and then the DNA content of the adherent cells was quantified fluorometrically by Hoechst 33258 fluorescence. Media was aspirated and the wells rinsed with Hanks Balanced Salt Solution (HBSS, phenol red free). The cells were sonicated in hypotonic media (0.1×HBSS) for 30 sec. The homogenate from each well was collected and Hoechst 33258 was added to a final concentration of 1 µg/ml. Fluorescence was measured on an SLM Aminco-Bowman series 2 luminescence spectrometer with a $\lambda_{ex}$ of 356 nm and a $\lambda_{em}$ of 492. Calf thymus DNA was used for calibration.

DETAILED DESCRIPTION OF THE INVENTION

In accordance with the present invention, methods and associated assays are described for the monitoring of the likelihood or onset of multidrug resistance in mammals, and the identification and monitoring of agents serving to alleviate the effects of multidrug resistance particularly in relation to the treatment of cancerous tumor cells.

The invention is predicated on an investigation of the role of pH in MDR. The results of this investigation indicate that the alkaline pH shift observed during multidrug resistance is sufficient to account for the observed decreases of cellular accumulation of chemotherapeutics. The studies presented later on herein include the measurement of pH accumulation in cells, as well as the accumulation of particular drugs that are limited in their dosage as a function of the alkalinization of the target cells under treatment.

In its broadest aspect, the diagnostic application of the invention is based on the observation that shifting intracellular pH is sufficient to either decrease the concentration of anti-cancer agents in drug-sensitive cells or increase their concentration in drug-resistant cells. Therefore it is a goal to find chemicals that re-acidify MDR cells and re-sensitize them to anti-tumor drugs. However, these chemicals must preferentially acidify MDR cells over normal cells in the body. The acidifying agents could then be coupled with anti-tumor drugs during chemotherapy.

One approach derived from the experiments underlying the invention is to load drug-resistant cell lines and tk normal cells with a pH indicator such as SNARF1. The pH of both cell types are then measured in response to a wide range of dosages of drugs that are used to modify cellular pH. There are two different strategies that will be used to select drugs for testing. Based on the observations on the mechanisms by which MDR proteins affect cellular pH, presented later on herein, drugs initially tested will be those that interfere with the ability of MDR proteins to affect cellular pH. However, given that the pH regulatory mechanisms of tumor cells are compromised relative to the regulatory mechanisms of normal cells, the large number of drugs that have been developed by the pharmacological industry to affect pH (primarily for the purpose of combatting ulcers) would also be tested. Using the equivalent of a fraction collector running in reverse (a fraction sipper) we can screen the effects of at least 10 drugs a day (with 10 different concentrations) on cellular pH for normal and MDR cells. The goal is to identify those drugs to which the MDR cells are more sensitive.

Manipulations that re-acidify MDR cells increase the accumulation of cytotoxic agents, and thereby facilitate their continued effective treatment. The strategy for identifying compounds that can reverse MDR depends upon finding drugs that have a greater effect on MDR acidification than on the acidification of normal, healthy cells. These drugs may be given in conjunction with normal chemotherapeutic agents to kill tumors. As described earlier herein, the approach to identify these compounds may be two-pronged:

A first targeted approach is to characterize the pH regulatory mechanisms of drug-sensitive and resistant cell lines. After the mechanisms that cause the alkaline shift have been characterized, they may be specifically targeted to find drugs that can preferentially acidify MDR cells.

A second scanning approach is predicated on the fact that many drugs have been identified that can affect the regulation of cellular pH. As previously described, MDR cells and normal cells would be loaded with a fluorescent dye sensitive to intracellular pH, after which aliquots of loaded cells would be dispensed into many different test tubes. The cells are then challenged with different concentrations of drugs which affect pH. A large number of samples can be quickly tested using a peristaltic pump coordinated with a spectrofluorimeter. This should give dose response curve for pH as a function of drug for both MDR and drug sensitive cells.

Tumor cells are compromised in their ability to compensate for the acid produced by metabolism—thus they are more acidic. MDR cells have managed to somewhat realkalinize their cytosol. However, these cells should be more vulnerable than healthy cells to drugs that perturb cellular pH.

After finding a drug that has a greater effect on acidifying MDR cells, the effects of these drugs will be tested on accumulation of the chemotherapeutic drugs. Since some of the key drugs (doxorubicin and daunomycin) are fluorescent, this can also be tested with a spectrofluorimeter. Next, after narrowing down the assay to a few key drugs, these will be tested on MDR and healthy cells growing in culture. Measurements will be made of growth rates and viability.

The next step is to combine the pH modulating or perturbing drug with the chemotherapeutic agents in treatments of tumors in mice, to confirm therapeutic efficacy.

In a further aspect of the invention, therapeutic methods and corresponding formulations are contemplated. For example, the agents identified by the assays of the present invention may be administered in conjunction with conventional chemotherapeutic agents, either individually or in a cocktail, or alternately in complex of the pH modulating agent and the chemotherapeutic. The complex may be prepared in pharmaceutical compositions that in turn, may be administered by those routes conventional for drugs of this type. For example the compositions may be administered by oral or parenteral means, such as intravenous.

The data presented in the following examples support the underlying concept of the invention that an additional mechanism of MDR by which changes in intracellular pH alter the transmembrane partitioning or intracellular sequestration of drugs. Cytosolic pH affects protonation of these drugs (typically weak bases, pKs between 7.4–8.2 (6–8)), affinity of intracellular sites for drug binding, and/or secretion from organelles which accumulate the drugs. The pH of tumor cells is considerably more acidic than that of normal (9) or MDR (10) cells. Drugs which partition across the membrane would be protonated and ionically trapped in the cytosol in their biologically active form (the charged form of these drugs binds to their targets such as DNA (11–15), RNA (15,16) and tubulin (17,18)). The acidic pH of tumor cells would increase their sensitivity to the drugs. The P-glycoprotein, as well as other proteins that are correlated with MDR, could affect the activity of chemotherapeutic agents by modification of pH homeostasis.

Gradients of pH have been used to trap these drugs in liposomes and red blood cells. To test whether the pH gradients observed in tumors and MDR significantly change intracellular drug concentration, we examined the kinetics of accumulation in drug-sensitive cells where the pH was manipulated experimentally to mimic that observed in resistant cells.

METHODS AND MATERIALS

Cells

NIH3T3 cells were grown at 37° C. in Dulbecco's Modified Eagle's Medium (DMEM) (Gibco Labs, MD) with 10% fetal calf serum (FCS) (Gemini Bioproducts, Inc, CA). NIH3T3 cell lines that were transfected with mdr-1 were supplemented with 100 nM vincristine sulfate. Myeloma cells (8226: the parental drug-sensitive line and DOX-40 the drug-resistant line) were grown in RPMI (Gibco, MD) with 10% FCS (Gemini Bioproducts). The drug-resistant line was supplemented with 100 nM doxorubicin-HCI (Calbiochem, CA). All media were supplemented with penicillin (Gibco Labs, MD), streptomycin (Gibco Labs, MD) and antimytopic (Gibco Labs, MD) with 2 mM L-glutamine (Gibco Labs, MD) and, unless indicated otherwise, maintained in 5% $pCO_2$.

Fluorescence and Confocal Microscopy

Fibroblasts (NIH3T3 cells) were grown on coverslips (VWR, 25 mm thickness 0.15 mm) which were placed in a Leiden coverslip chamber (Medical Systems, NY). Myeloma cells were adhered to the same coverslips with Cell-Tak (Collaborative Biomedical Products, Becton Dickinson, Mass.) according to the manufacturer's instructions. The chamber and solutions were kept at 37° C. Solutions equilibrated with ambient (0.033%), 2%, 5% or 10% $CO_2$ perfused at a constant velocity. Warmed air (at appropriate $pCO_2$) was perfused across the surface.

Fluorescence microscopy

The coverslip chamber with the cells was mounted on an Nikon Diaphot inverted microscope and illuminated with a 100 W Hg Lamp (Nikon) with a 97% neutral density filter. For quantification of cell-associated fluorescence, the chamber was mounted on a Zeiss Axiovert 135 inverted microscope with a 100 W Hg light source and a 97% neutral density filter and a Hamamatsu cooled CCD camera #C4880.

Confocal microscopy

The chamber was mounted on an inverted InSight Confocal Microscope (Meridian Instruments, Okemos, Mich.) which used an argon laser for excitation at 488 nm.

Chemicals

Daunomycin (Calbiochem, CA) and doxorubicin (Calbiochem, CA) were made as a 10 mM stock in water and stored at 4° C. SNARF1-AM (Molecular Probes, OR) was stored as a 20 mM stock in anhydrous DMSO (Aldrich, Wis.) and stored at −20° C.

pH measurement

The pH of cells was measured using SNARF1-AM (Molecular Probes, OR) according to the manufacturer's instructions. Fibroblasts grown on cover slip dishes in DMEM with 10% FCS were rinsed in DMEM without FCS, and then incubated in DMEM with 10 μM SNARF1-AM for fifteen minutes. The cells were then placed on an InSight and excited at 488 nm with emission recorded at 570/30 nm and 630/lp nm. A pH calibration curve was constructed by rinsing the cells with 150 mM KCl with 6 μM nigericin and 50 mM sodium phosphate buffered to pH 6.6, 6.8, 7.0, 7.2, 7.4, 7.6, 7.8 and 8.0. Myeloma cells were harvested and then resuspended in medium without FCS. SNARF1-AM was added to a final concentration of 10 g/ml for fifteen minutes at 37° C. The cells were then placed in a dialysis bag (SPECTRAPOR, Fisher Scientific, MW cutoff 12,000–14,000, 1.6 cm diameter) suspended in a 200 ml beaker with RPMI. The RPMI in the beaker was maintained at 37° C. and kept aerated with an aquarium airstone with 0.03%, 2%, 5%, or 10% $CO_2$ in air. The stirred bathing medium could be changed to vary the concentrations of $CO_2$ or drugs in the dialysis bag. For measurement in a spectrofluorometer an emission scan was taken from 520–700 nm with excitation at 488 nm and 514 nm. The cells were calibrated, as described above for the fibroblasts, for both excitations and the results at each was compared. For measurement on a fluorescence activated cell-sorter (FACS, Becton-Dickerson FACSTAR$^{PLUS}$, MA) the cells were pumped at 0.38 ml/min with an Ismatec peristaltic pump (Cole-Parmer, Ill.) and excited with an argon laser at 514 nm and emission was monitored with filters at 570/26 nm and 630/30 nm. For measuring daunomycin concentration the cells were excited at 488 nm and emission monitored at 570 nm.

EXAMPLE 1

Daunomycin accumulates in cells

Daunomycin, a chemotherapeutic agent, fluoresces maximally at 595 nm when excited at 488 nm. These optical properties enable monitoring the drug in living cells. NIH3T3 fibroblasts were incubated in the presence of 5 M daunomycin for 30 minutes and examined on an inverted fluorescence microscope. Since the fluorescence spectrum of daunomycin is not affected by pH (data not shown), the fluorescent images of increasing cytosolic daunomycin fluorescence reflect accumulation of the drug. The concentration of daunomycin in the cytosol (FIG. 1) is higher than in the surrounding media, with the highest concentration in the nucleoli and two of the major acidic compartments of the cell (trans golgi and lysosomal), as has been previously reported (19). Similar patterns of intracellular accumulation were observed for cells incubated with doxorubicin and with several strains of NIH3T3 fibroblasts and with myeloma cells growing in suspension. Daunomycin binds DNA with great affinity and to a lesser extent RNA (15,16). Binding to tightly packed DNA in the chromatin results in quenching of the daunomycin fluorescence while binding to nucleoli yields fluorescent structures.

EXAMPLE 2

The pH is different in drug-sensitive and drug-resistant cells:
The NIH3T3 fibroblasts and myeloma cells were loaded with SNARF1-AM, a dye whose fluorescence emission is pH-sensitive. When excited at 514 nm, its emission maximum is at 630 nm in a basic environment and at 570 nm when acidic. Ratioing of fluorescence emission is used as a quantitative measure of the pH, independent of cell volume or dye concentration. The pH of the myeloma cells, as measured in a FACS or spectrofluorimeter, was 7.1 for the drug-sensitive cells (8226) and 7.45 for the drug-resistant cells (DOX-40). The pH of the drug-sensitive NIH3T3 cells (mock transformed with a neomycin marker) was 6.8 while that of those transfected with mdr-1 was 7.25 as measured with a fluorescence confocal microscope.

EXAMPLE 3

Changing the $pCO_2$ rapidly and reversibly shifts cytosolic pH

To mimic the alkaline cellular pH shift that occurs in MDR, the $pCO_2$ was lowered. $CO_2$ quickly equilibrates across cellular membranes. The rapid activity of cytosolic carbonic anhydrase and the numerous cellular mechanisms to regulate bicarbonate exchange ensures that changes of $pCO_2$ rapidly affect cellular pH (20). NIH3T3 fibroblasts were loaded with SNARF1-AM and mounted on an inverted microscope. Changing the $pCO_2$ from 5% to 2% resulted in a rapid alkaline shift of intracellular pH in the fibroblasts from 6.8 to 7.2. This pH shift was reversible, changing the $pCO_2$ back to 5% returned the pH to 6.8. The basal pH value of 6.8 is somewhat more acidic than previously reported values for the NIH3T3 cells. However, in those experiments, pH was measured with the cells at an ambient $pCO_2$ of 0.033%. The pH rises as the $pCO_2$ is changed from 5% to 0.033% (21). The results are consistent with published measurements in 5% $pCO_2$ (22).

The pH of myeloma cells, grown in suspension, was examined in both a FACS and in a spectrofluorometer. The emission spectrum of SNARF1 in drug-sensitive cells (black line in FIG. 2a) and MDR cells (FIG. 2a gray line) is shown at a $pCO_2$ of 5% (solid line) or $pCO_2$ of 2% (dashed line). The pH of sensitive cells incubated with a $pCO_2$ of 2% (measured as the ratio of the emission at 630 nm to 585 nm, FIG. 2a dashed black line) was indistinguishable from the pH of the resistant cells at a $pCO_2$ of 5% (solid grey line). This demonstrates that varying $pCO_2$ can be used to shift the pH of the drug-sensitive cells to a value as alkaline as the resistant cells. Likewise, the pH of the drug-sensitive cells in 5% $CO_2$ (FIG. 2b) was comparable to the pH in resistant cells at a $pCO_2$ of 10% (FIG. 2b). Alternatively, the resistant cells could have their intracellular pH shifted to that of the more acidic sensitive cells.

The pH of the drug-sensitive myeloma cells was 7.1 and that of the drug-resistant cells in 5% $pCO_2$ was 7.45. The $pCO_2$ was modified in the following manner: 5%, 2%, 0.03%, 2%, 5%, 10%, 5%. The pH values were measured for each level of $pCO_2$. At a lower $pCO_2$, the intracellular pH was more alkaline and at higher $pCO_2$ more acidic. At a $pCO_2$ of 2%, the pH was 7.45 for the sensitive cells and 7.75 for the resistant cells. This was accompanied by a shift of only 0.04 pH units in the extracellular pH. Cells at 0.03% $pCO_2$ demonstrate pH of 7.85 (sensitive) and 7.9 (resistant). Returning the cells to a $pCO_2$ of 5% caused the pH to rapidly revert to the starting level. Further, increasing the $pCO_2$ to 10% caused an increased acidification to 6.65 (sensitive) and 7.05 (resistant). This sequence of cycling $pCO_2$ was repeated each time yielding the same intracellular pH values shown in FIG. 2b.

EXAMPLE 4

Figure 3A:
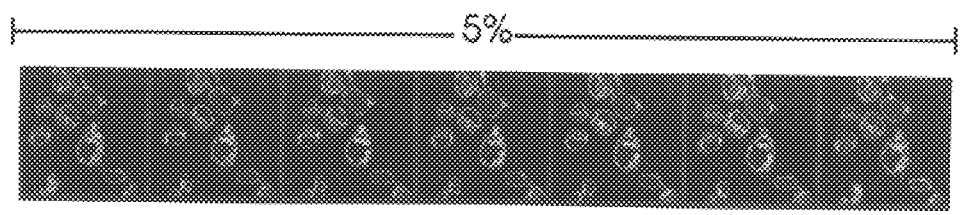
FIG. 3A–3H demonstrate the effect of shifting $pCO_2$ on the daunomycin fluorescence in NIH3T3 cells. Fibroblasts were incubated in 2 $\mu$M daunomycin and excited at 488 nm and emission recorded at 570 nm every 15 sec. The medium initially was equilibrated with 5% $pCO_2$ (The first 7 frames—red background). The $pCO_2$ was shifted to 2% for 2 min. (blue background) and there was a substantial decrease in the cellular daunomycin fluorescence. Upon returning to 5% $pCO_2$ (red background) the cellular daunomycin fluorescence returned. The cells were repeatedly cycled between 5% $pCO_2$ (red background) and 2% $pCO_2$ (blue background). The daunomycin concentration is pseudocolored with the lowest level in black and increasing concentrations in blue, green, red and yellow.
Figure 3B:
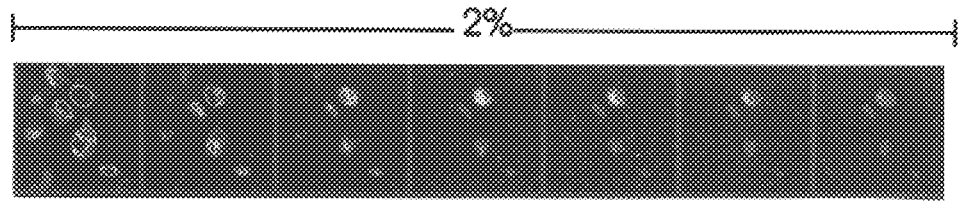
Figure 3C:
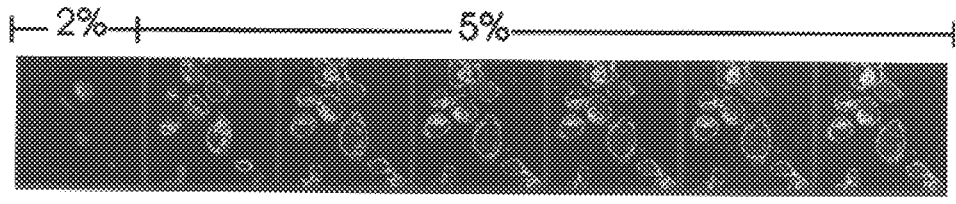
Figure 3D:
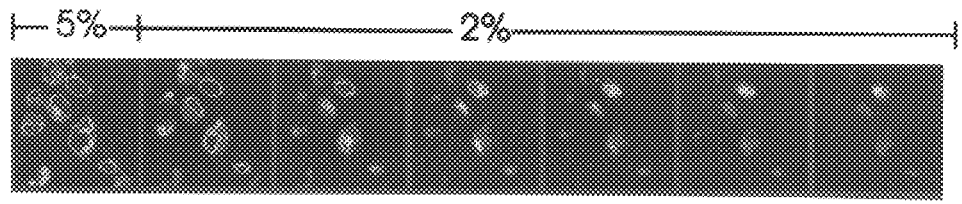
Figure 3E:
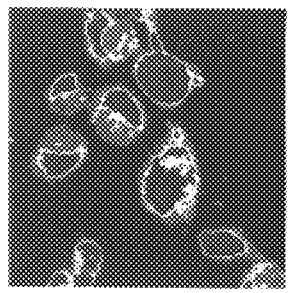
Figure 3F:
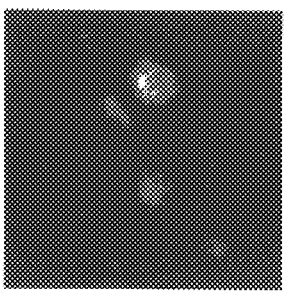
Figure 3G:
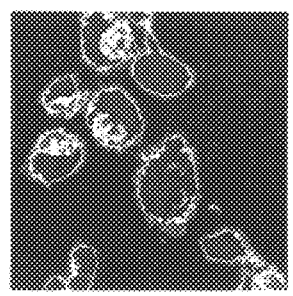
Figure 3H:
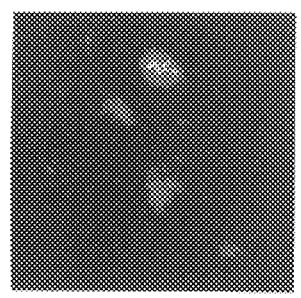
Figure 3I:
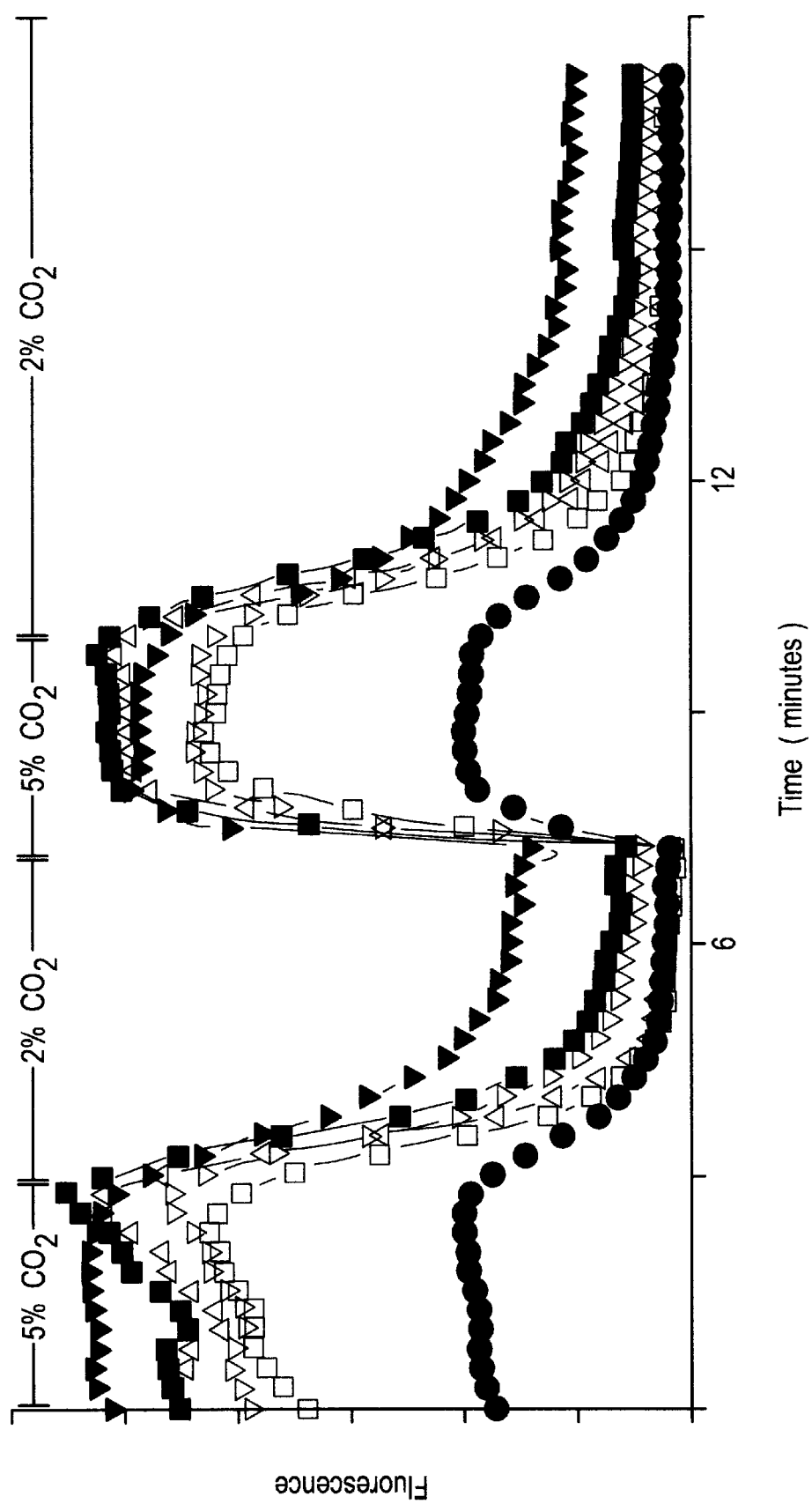
FIG. 3I demonstrates the quantification of the effect of pCO2 on daunomycin fluorescence in NIH3T3 cells (from FIG. 3a) The daunomycin fluorescence was quantified for six different cells as the $pCO_2$ was shifted between 2 and 5%. Reducing the $pCO_2$ raises the cytosolic pH and reduces the cell-associated daunomycin fluorescence. These effects are completely reversible and can be repeated on the same cells many times.

Changing $pCO_2$ rapidly and reversibly shifts intracellular daunomycin fluorescence NIH3T3 cells at 5% $pCO_2$ were incubated with 5M daunomycin until the intracellular levels were approximately at a steady-state (FIG. 3a, red background). The $pCO_2$ perfusing the solution was shifted from 5% to 2% (FIG. 3a, blue background). The daunomycin fluorescence rapidly decreased in the cells. Upon returning the cells to 5% $pCO_2$ (red background), the daunomycin fluorescence increased to its starting level. The pattern remained unchanged upon repeated cycling between 2% and 5% $pCO_2$. The intracellular daunomycin fluorescence was quantified for a number of cells (FIG. 3b). In all cases, the cellular fluorescence decreased when the $pCO_2$ was lowered (more alkaline pH) and the fluorescence increased when the $pCO_2$ was increased. These changes were rapid, repeatable and reversible.

The experiment was repeated with both drug-sensitive (8226) and resistant (DOX-40) myeloma cells with similar results. Cells were loaded with 20M daunomycin in medium equilibrated with 5% $pCO_2$. While monitoring the daunomycin fluorescence, the $pCO_2$ was sequentially shifted to 2%, 0.03%, 2%, 5%, 10% and 5% (FIG. 4a). This cycle was repeated. The cellular daunomycin fluorescence decreased when the $pCO_2$ was lowered (which shifts the pH alkaline) and increased when the $pCO_2$ was raised. These changes were completely reversible and occurred at the same rate in all intracellular compartments.

Similar reversible increases of cellular drug levels were also observed when the pH was transiently shifted alkaline with 20 mM $NH_4Cl$ for 2 minutes (data not shown). Reversible increases of cytosolic drug levels were observed when the pH was transiently shifted acidic with 2.5 mM $NaN_3$ for 2 minutes (data not shown).

DISCUSSION

Fluorescent chemotherapeutic agents accumulate in tumor cells (see FIG. 1). This could be a consequence of decreased drug influx, increased intracellular trapping and/or increased drug efflux. There are two general mechanisms for drug transport: active and passive. An active transport model for MDR has been proposed based on the observations that transport is blocked by metabolic inhibitors such as azide and that transport is associated with the expression of the P-glycoprotein, an ATP binding protein which is a member of a family of membrane transporters.

The passive diffusion models are based on the observation that these drugs are sufficiently hydrophobic to cross membranes. The asymmetric distribution of the drugs is assumed to be the consequence of an asymmetry of chemical potential (such as pH, voltage and ionic concentrations). For example, the higher rate of aerobic glycolysis in tumors and the hypoxic conditions surrounding cells within a tumor mass cause an acidic environment (9). This increased proton concentration has two effects. First, the drugs that are weak bases will be protonated and trapped in the cytosol. Second, the binding of each of these drugs to their cytosolic targets, such as tubulin (17,18) or DNA (11-15), has an acidic pH optimum. Conversely, an increased pH both decreases intracellular drug accumulation and reduces binding to intracellular targets.

Passive transport of drugs in conjunction with a trapping mechanism is consistent with a number of independent observations. First, in simple systems such as red blood cell ghosts (23) and phospholipid vesicles (24) the transmembrane distributions of these drugs is determined by the pH.

Second, the cytosolic pH of tumor cells increases with increased MDR (25). Third, transfection of cells with the P-glycoprotein causes an alkaline shift of cytosolic pH (10). Fourth, verapamil, which reverses MDR, partially reverses this shift of cytosolic pH (25). Verapamil increases the concentrations of anti-cancer drugs even in cells which do not express P-glycoprotein (26,27). Fifth, drug influx is slower in resistant cells (4,28–36) which is consistent with differences in the rate of trapping and inconsistent with an active efflux model. Sixth, drugs which acidify the cytosol such as amiloride reverse MDR (37).

As shown, the passive trapping hypothesis can account for changes in cellular accumulation of chemotherapeutic agents that are weak bases. What about the rest? None are negatively charged but some, such as colchicine, are neutral. Each of these drugs has an intracellular target. Binding of colchicine to its target, the extremely acidic carboxy terminus of tubulin (38) is pH dependent with an optima of pH 6.7–6.8 (39). Any alkaline shift of the pH decreases the binding of colchicine and could protect the cell from this chemotherapeutic agent. Multiple forms of non-P-glycoprotein MDR have been observed. The passive transport theory predicts that each affects a common feature—regulation of cellular pH. One protein responsible for non-P-glycoprotein-mediated MDR has recently been cloned and demonstrated to be a vacuolar $H^+$-ATPase subunit (1). Other mechanisms for MDR may use pH to affect drug distribution either by selective sequestration, i.e. drug uptake by lysosomes, or modifications in the secretory pathway (40). Consistent with this hypothesis is the observation of an increase in non-specific adsorptive endocytosis in anthracycline- and vinca alkaloid-resistant cells (41), as well as an increase in membrane traffic in daunomycin-resistant cells (42). In drug-resistant cells, there is a significant rate of exocytosis of lysosomal enzymes, suggesting a modification of the endocytic pathway. Furthermore, an enhanced rate of exocytosis of vesicles containing a H+-ATPase could be a means by which cytosolic pH is raised, as has been observed in plant and animal cells (43,44).

These results demonstrate the passive trapping model is sufficient to account for the enhanced sensitivity of tumors to anti-cancer drugs and the decreased sensitivity in MDR. When the pH of drug-sensitive cells is shifted to the level observed in drug-resistant cells, they no longer accumulate chemotherapeutic agents. Likewise, when drug-resistant cells are shifted to the level observed in drug-sensitive cells, they accumulate chemotherapeutics. Although, our results neither directly prove nor disprove the hypothesis that the P-glycoprotein is an ATP-driven drug efflux pump or flippase they demonstrate the existence of alternate pathways for MDR.

As described in detail above, there are a number of potential therapeutic implications from this work. If tumor cells are compromised in their ability to regulate pH, they may be more susceptible than healthy cells to pharmacological approaches that modify pH regulation. Thus, approaches that affect pH may potentiate the effects of the chemotherapeutic agents and, in this manner, reverse MDR.

EXAMPLE 5

Acidification of intracellular compartments is essential for correct sorting and transport of proteins during endocytosis and secretion. Here we report that a human breast cancer line (MCF-7) is aberrant in acidification of intracellular vesicular compartments. This defect is correlated with a disruption in the organization and function of the trans-Golgi network (TGN) and the pericentriolar recycling compartment. In marked contrast, human breast cancer cells (MCF-7adr) that are resistant to the most widely employed chemotherapeutic drug, adriamycin, appear normal in both acidification of intracellular vesicular compartments and in the organization of the recycling and secretory compartments. Treatment of drug resistant MCF-7adr cells with nigericin and monensin, ionophores demonstrated to disrupt vesicular acidification (48), results in a resensitization of these cells to adriamycin. Drug sensitivity is proposed to result from an acidification defect within vesicles of the recycling and secretory pathways. The functional consequence of this defect is the diminished capacity of cells to remove drugs from the cytosol through vesicle mediated protonation, sequestration, and secretion of cytotoxic drugs.

Cancer cells are more sensitive to chemotherapeutic drugs than normal cells. The development of drug resistance in tumors treated with chemotherapeutics is accompanied by changes in cell physiology. This includes overexpression of numerous cellular proteins, changes in the subcellular distribution of the chemotherapeutics and an alkaline shift of cellular pH. It has been suggested that the alkaline shift could be causally related to drug-resistance. Most of the chemotherapeutics are weak bases with pKs of 7–8. Thus, they would be expected to accumulate in tumor cells which are more acidic than normal, or drug-resistant cells (52). The pH difference between drug resistant tumor cells and their parental cell lines is sufficient to quantitatively account for the decreases in drug-accumulation observed in drug-resistant cells (52). However, it has recently been reported for one particular cell line, the MCF-7 breast cancer cell, that the pH difference is only 0.2 between the drug-resistant and drug-sensitive cells (Altenberg, 1993). This is too small a pH gradient to account for the differences in cellular drug accumulation.

Here we describe structural and functional alterations within MCF-7 and MCF-7adr cell lines that are correlated with either enhanced drug sensitivity or resistance. These differences are observed as changes in: (a) the organization of the secretory compartment, TGN, (b) the activity and organization of the endosomal/pericentriolar recycling compartments, (c) secretion of lysosomal enzymes, and (d) the cytoplasmic and vesicular pH. Each of these cellular changes could be affected by a disruption of the acidic gradients in the TGN and recycling endosome.

In agreement with the previous report (Altenberg, 1993), we observed that the total cellular difference of pH between the MCF-7 and MCF-7 adr cells is only 0.3 pH units. However, there were substantial differences in subcellular pH. Specifically in the MCF-7 cells, there is a complete absence of subcellular pH gradients. In contrast, the drug-resistant MCF-7adr cell line has restored pH gradients. The cytosolic pH of the MCF-7adr cells is significantly more alkaline than the cytosolic pH of the MCF-7 cells and the organellar pH is significantly more acidic in the MCF-7adr cells. Thus, as with all other drug-resistant cell lines, chemotherapeutic drugs are excluded from the cytosolic compartments by pH gradients. Drugs that reach the cytosol are trapped in the acidic secretory pathway and rapidly passed from the cell. Disrupting the pH gradients of the secretory pathway reversed the drug-resistance of the cells.

Experimental Procedures

Reagents

Acridine orange was purchased from Aldrich (Milwaukee, Wis.). The fluorescent reagents, Bodipy-ceramide, the acetoxymethylesters of both carboxy SNARF and SNAFL-calcein, and Bodipy-lactalbumin, were from Molecular Probes (Eugene, Oreg.). Adriamycin was from Calbiochem (La Jolla, Calif.). Monensin and nigericin were from Sigma (St. Louis, Mo.).

Tissue culture

Cells were seeded and grown in Dulbecco Modified Eagle's (DME) media containing 10% fetal calf serum (phenol red free) in Lab-Tek culture chambers (Nunc, Naperville, Ill.) maintained in an incubator at 37° C. and 5% $CO_2$. Human breast cancer cells (MCF-7) and the adriamycin resistant line (MCF-7adr) were obtained from Dr. William W. Wells of the Department of Biochemistry, Michigan State University. The media for the MCF-7adr cells was supplemented with adriamycin (0.5 µg/ml). Cells were utilized 3–4 days following plating.

Confocal fluorescence imaging of intracellular pH and acidic compartments

Acridine orange (2 µg/ml media; 4 mg/ml stock in water) was added directly to the chambers and the cells were incubated with the dye at 37° C. for 30 minutes. Cells in the presence of acridine orange were then examined at room temperature with an Insight Bilateral Laser Scanning Confocal Microscope (Meridian Instruments, Okemos, Mich.). Excitation was at 488 nm (argon ion laser beam) and dual emission confocal images were sequentially recorded utilizing both a 530-30 band pass barrier filter (green fluorescence) and a 605 nm long pass barrier filter (red fluorescence). Acridine orange demonstrates a concentration dependent long wavelength shift in the fluorescence emission; it shows a red fluorescence when accumulated to a high concentration within acidic cellular compartments and a green fluorescence when bound at lower concentration to membranes and/or nucleic acids. Optical sections of the fluorescent sample were recorded at 0.5 micron intervals. Typical individual sections are presented to demonstrate the distribution of acridine orange within the cytoplasmic and vesicular compartments. The acetoxymethylester derivative of SNAFL-calcein (15 µg/ml) (Molecular Probes, Eugene, Oreg.) (a ratiometric fluorescent probe for pH) was added to both MCF-7 and MCF-7adr cells. The ester linked fluorescent probe enters the cell passively where the esters are hydrolyzed by esterases located in the cytoplasm and intracellular vesicles. The SNAFL-calcein is then ionically trapped within the cytoplasm and vesicular compartments. The cells were incubated at 37° C. for 45 minutes and then examined with the Insight confocal fluorescence. Optical sections were obtained utilizing two different filter settings for emission (530-30 band pass barrier filter and 630 long pass filter) and a single excitation wavelength (488 nm) as previously described for carboxy SNARF-1 (52). The pixel intensities obtained at the two different emission intensities were divided to obtain a ratio image of the internalized pH probe (52). These images were then compared to standard curves that were obtained in the following manner. To obtain a quantitative relationship between emission ratios and pH, each SNAFL-calcein stained cell line was exposed to a buffer at a known pH containing nigericin/high $K^+$ (18 (M/150 mM KCl) (52). This treatment equilibrates all the internal compartments of the cell to the pH of the incubating buffer. By sequentially changing the pH buffer that is bathing the cells, a pH curve was generated for each cell line that demonstrated the relationship between the SNAFL-calcein fluorescence emission ratio and pH. These values were then incorporated into a pH imaging routine that provides a direct read-out of pH values for individual intracellular compartments that are queried on the computer screen. Cells treated with monensin were exposed to the drug (10 µg/ml of media) for 30 minutes at 37° C. prior to labeling with SNAFL-calcein as described above. All cells were examined at room temperature.

Figure 5C:
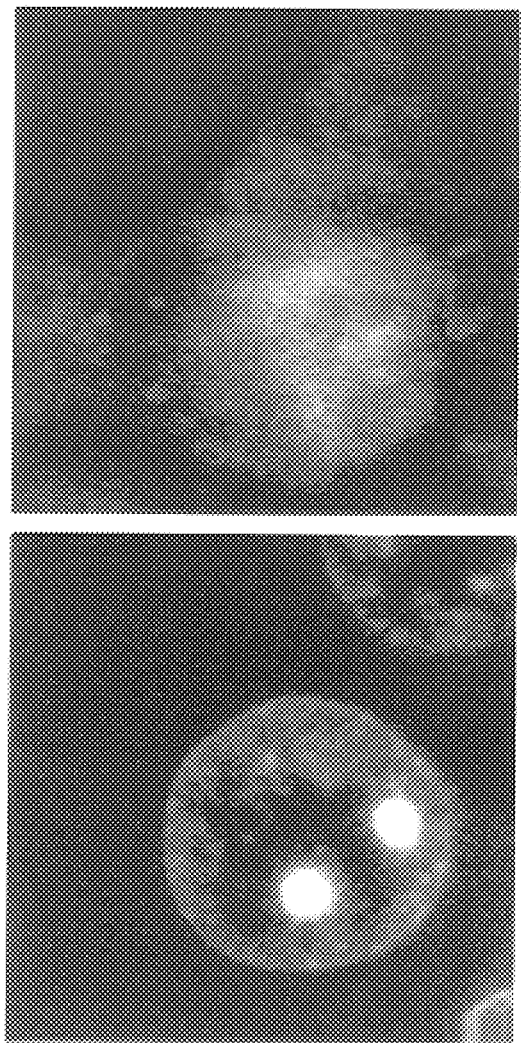
Figure 5D:
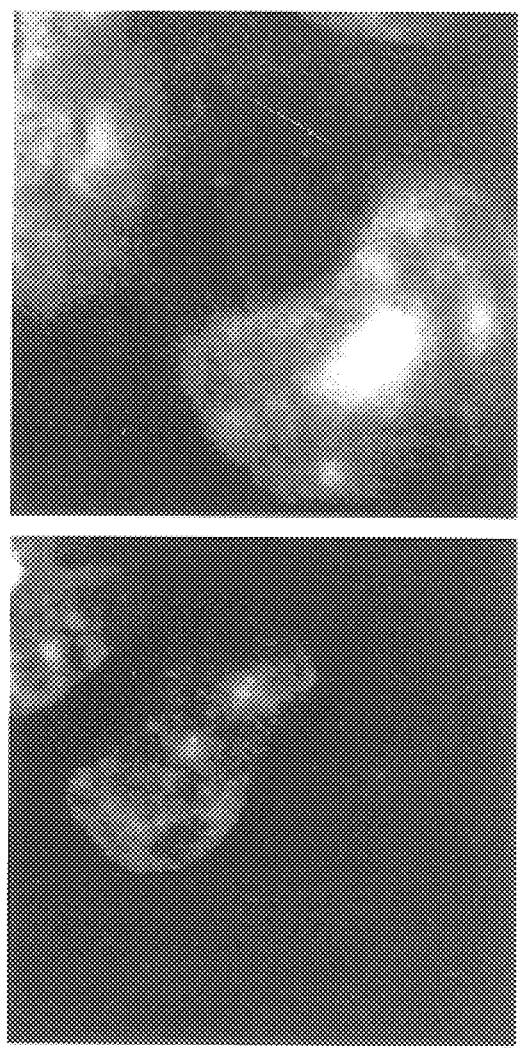

Fluorescence labeling and confocal imaging of endosomal and secretory compartments Bodipy-ceramide (Bodipy-Ceramide; Molecular Probes, Eugene, Oreg.) has been demonstrated to label Golgi compartments. Conversion of Bodipy-ceramide to Bodipy-sphingomyelin (in cis-Golgi) is associated with the movement of the newly synthesized fluorescent lipid to the trans-Golgi network (TGN). As the Bodipy-sphingomyelin concentration increases within the TGN and secretory vesicles, a long wavelength shift in fluorescence occurs that results in red fluorescent structures (TGN and secretory vesicles) against a green fluorescent background. Cells were incubated with Bodipy-ceramide (3 µg/ml) for 15 minutes at 37° C., washed once with fresh media and then examined in optical section at room temperature with confocal fluorescence microscopy. Excitation was at 488 nm and dual emission images were prepared utilizing the filter set described for acridine orange (FIG. 5). To examine internalization, Bodipy-lactalbumin (Bodipy-Lac, Molecular Probes, Eugene, Oreg.) was used as a fluid phase marker. Cells were incubated with Bodipy-Lac (2 mg/ml) for 90 minutes at 37° and then washed once with cold media and rapidly examined with confocal fluorescence microscopy (($_{ex}$=488 nm, ($_{em}$530-30 nm band pass filter).

Cell viability assays

The media was removed 60 hr. after plating the cells and replaced with fresh media supplemented with various concentrations of adriamycin (Calbiochem, CA) and monensin (solubilized in DMF 0.1%) (Sigma, St. Louis). After 6 hr the media was removed, the cells rinsed, and then fed with fresh media not containing drugs. The cells were fed daily for three days and then the DNA content of the adherent cells was quantified fluorometrically by Hoechst 33258 fluorescence. Media was aspirated and the wells rinsed with Hanks Balanced Salt Solution (HBSS, phenol red free). The cells were sonicated in hypotonic media (0.1×HBSS) for 30 sec. The homogenate from each well was collected and Hoechst 33258 was added to a final concentration of 1 µg/ml. Fluorescence was measured on an SLM Aminco-Bowman series 2 luminescence spectrometer with a $\lambda_{ex}$ of 356 nm and a $\lambda_{em}$ of 492. Calf thymus DNA was used for calibration.

Results and Discussion

The fluorescent pH sensitive probe carboxy SNARF-1 (acetoxymethylester form) (50) (Molecular Probes, Eugene, Oreg.) was employed to measure the intracellular pH in both MCF-7 and MCF-7adr cells. This probe partitioned within the cytoplasm of both cell lines. The cytoplasmic pH for MCF-7 cells was 6.8±0.1 (10 cells, 3 separate confocal sections) and for MCF-7adr cells 7.1±0.1 (10 cells, 3 separate confocal sections) (Table 1) consistent with other published measurements reporting a more acidic cytoplasm for drug sensitive cells (49). The more acidic cytoplasmic pH measured in MCF-7 cells suggested that the drug sensitive cells were manifesting an aberrant regulation of intracellular pH that might be representative of other changes in pH within intracellular vesicular compartments. This was examined with acridine orange, a probe previously employed to determine the presence of acidic intracellular compartments (51). As observed in FIG. 5, MCF-7 cells have few orange stained vesicles within the cytoplasm (FIG. 5, top row left). In sharp contrast, intensely red stained vesicles are observed in MCF-7adr cells in both the pericentriolar region of the cytoplasm and dispersed throughout the cytoplasm (FIG. 5, top row right). Treatment of either cell type with nigericin (7.5 (M) eliminated fluorescent staining of both cytoplasmic vesicles and vesicles within the pericentriolar region (FIG. 5, second row).

To quantify the pH in intravesicular compartments we used the fluorescent pH probe SNAFL-calcein (acetoxymethylester form) (50) (Molecular Probes, Eugene, OR). SNAFL-calcein was observed to differentially localize within the two cell types. In MCF-7 cells, the probe was shown to distribute predominantly in the cytoplasm of cells with accumulation in a few vesicles (FIG. 5, bottom row left). Again, in sharp contrast, little cytoplasmic labeling was observed in the MCF-7adr cells (FIG. 5, bottom row right), but considerable vesicular labeling was demonstrated particularly in the pericentriolar region. This was also observed for staining of MCF-7adr cells with acridine orange (FIG. 5, top row). To quantify the pH within these vesicular compartments, the fluorescence emission ratio of SNAFL-calcein was determined for individual vesicles within a population of MCF-7 and MCF-7adr cells (20 cells per cell type) (52). These values were then compared to a standard curve (see legend to FIG. 5). As shown in the pH histogram (FIG. 6, Table 1), the vesicular compartments are significantly more acidic in MCF-7adr cells than in the sensitive MCF-7 cells; further, the pH gradients between the cytoplasm and the lumenal compartments is considerably larger in MCF-7adr cells (Table 1).

These measurements indicate that drug sensitive MCF-7 cells do not contain appropriately acidified late endosomes (pH 5.2–5.8), sorting endosomes (pH ~6.0), endosomes (pH ~6.0–6.3) (45-47), or secretory vesicles (pH ~5.8) (54). Thus, the MCF-7adr line more closely resembles normal, non-tumor cells, in this regard. We examined the possibility that the aberrant vesicular pH observed in MCF-7 cells is reflected in altered organization and activity of these compartments. Bodipy-ceramide (Bodipy-Ceramide) (Molecular Probes, Eugene, Oreg.), a fluorescent marker for the trans-Golgi network and secretory vesicles, showed a dispersed tubulo-vesicular distribution in MCF-7 cells (FIG. 7a) (55). A large number of vesicular and cisternal structures appeared to be interconnected and possibly budding from a thin reticular network (enlarged image in FIG. 7b). In contrast, MCF-7adr cells labeled with Bodipy-Ceramide demonstrate asymmetrically localized pericentriolar structures characteristic of the trans-Golgi network (FIG. 7c). In addition, small labeled secretory vesicles (arrows) were found within the cytoplasm (FIG. 7d). Such vesicles were not easily detected in the MCF-7 cells (FIG. 7a). The organization and activity of the pericentriolar recycling compartment (46) was examined with Bodipy-lactalbumin (Bodipy-LAC; Molecular Probes, Eugene, Oreg.), which was used as a fluorescent fluid phase marker. Steady state labeling of MCF-7 cells (FIG. 7e) showed uptake of fluorescent protein into peripheral vesicular compartments. No accumulation or aggregation of fluorescent vesicles was observed in association with a compartment within the pericentriolar region of the cytoplasm. In contrast, MCF-7adr cells (FIG. 7f) showed fluorescent vesicles associated with a labeled pericentriolar compartment.

Figure 6A:
Figure 6B:
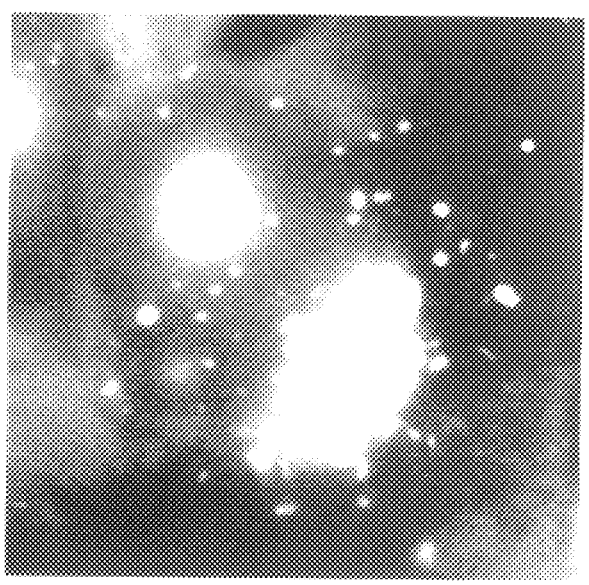

These observations suggested that the sensitivity of drug resistant cells to adriamycin might be overcome by chemically interfering with the capacity of these cells to acidify the vesicles that mediate internalization and secretion. As demonstrated in FIG. 8, addition of monensin to MCF-7adr cells at non-cytotoxic concentrations increased the drug sensitivity of the MCF-7adr cells to the level observed for drug-sensitive cells. The enhanced drug sensitivity of MCF-7adr cells treated with monensin was directly correlated to an alkalization of acidic vesicular compartments to pH values observed for drug sensitive MCF-7 cells (FIG. 6). Nigericin and amiloride functioned in a similar manner (data not shown). These changes did not result from disruption of the Golgi since Brefeldin A (which breaks down the Golgi, but does not disrupt transport from the trans-Golgi or CURL to the cell surface (56) did not affect drug sensitivity (data not shown).

Organelle acidification affects intracellular targeting, e.g. fusions of endosomes, secretory vesicles, and lysosomes; uncoupling of ligands from membrane receptors; processing and degradation of proteins; targeting of lysosomal enzymes; and glycosylation and packaging of secretory glycoproteins/glycolipids (45–47). This communication demonstrates that the human breast cancer cell line (MCF-7) is defective in both the acidification of intracellular vesicles (FIG. 5) and the organization of the pericentriolar recycling compartment and the TGN (FIG. 7). These abnormalities appear repaired in the adriamycin resistant variant of this cell line (MCF-7adr). The role of a collapsed trans-vesicular pH gradient as the primary factor in producing drug sensitivity was strongly supported by results with ionophores. Monensin and nigericin enhanced the drug sensitivity of adriamycin resistant cells (MCF-7adr).

A mechanism for the pH shift observed in this study is suggested from work on parallel systems that show a similar shift in the lumenal pH of intracellular organelles. In endocytotic and secretory compartments an electrogenic ATPase coupled to a Cl(conductance is responsible for maintaining the low pH (51, 53, 57). In cystic fibrosis, a decreased chloride conductance in the trans-Golgi compartment and recycling endosomes causes an alkaline shift of organellar pH (51, 57). In the absence of chloride, the lumenal pH shifts 0.4–0.6 units alkaline in multivesicular bodies (MVB), CURL vesicles, and receptor recycling compartments (53).

Analogously, an aberrant chloride conductance in the organelles of MCF-7 cells may cause the alkaline pH shift which is similar in magnitude to those observed in the previously cited examples (see Table 1). Likewise, the activation of a chloride conductance, or expression of a Cl⁻ conductance channel, in the MCF-7adr cells may then normalize the pH within acidic compartments. Adriamycin and a large number of drugs utilized for chemotherapy are weak bases which can be protonated and, thus, trapped in acidic compartments. Drug sensitivity of MCF-7 cells may be a consequence of an inability to protonate, sequester and then secrete these drugs (PSS model). Drug resistance is then an "ionic rehabilitation" of the normally acidic intracellular compartments through the expression of proteins (e.g. chloride channels or proton pumps) that compensate for this defect in acidification within tumor cells. One candidate protein for acidic rehabilitation is the p-glycoprotein which is expressed in many drug resistant cells, including the MCF-7adr. P-glycoprotein has been reported to function as a Cl channel (58) or modify chloride conductance and is observed in the Golgi, vesicular and plasma membranes (59, 60).

While multidrug resistance is likely to be the consequence of diverse mechanisms (49), the ability to reverse drug-resistance by drugs that alkalinize the pH in acidic compartments of the endosomal and secretory systems indicates that protonation, sequestration and secretion are the principle elements of the primary mechanism for drug resistance in the MCF-7 breast cancer line. Any manipulations that either affect acidification or transport through these organelles should affect drug-sensitivity. It is possible that the Golgi, particularly the secretory compartments, may normally play a role in protecting all cells from environmental toxins that are weak bases.

EXAMPLE 6

Tamoxifen Reverses Drug Resistance in MCF-7 Cells. Defective acidification within exocytotic compartments in adriamycin-sensitive MCF-7 human breast cancer cells is correlated with fragmentation of the trans-Golgi network (TGN) and disruption of the pericentriolar recycling compartment (PRC). These defects are repaired in drug resistant cells (MCF-7adr). This report demonstrates that brief treatments of drug resistant MCF-7adr cells with tamoxifen reverts their phenotype to resemble the drug-sensitive cells including: (a) disruption of the structure of the TGN and PRC, (b) loss of acidification in exocytotic compartments, (c) redistribution of adriamycin from exocytotic compartments to the nucleoplasm, and (d) increased sensitivity to chemotherapy. Reversal of drug-resistance is proposed to result from tamoxifen mediated inhibition of acidification within exocytotic compartments.

Treatment of tumors with chemotherapeutics can result in the appearance of cells displaying an acquired drug resistance to a spectrum of drugs. This resistance is termed multidrug resistance (MDR) (49). We have recently demonstrated that intracellular vesicular compartments do not acidify in drug sensitive MCF-7 human breast cancer cells (62) but do acidify normally in drug resistant cells. This "ionic rehabilitation" of intravesicular pH in resistant cells could greatly facilitate the protonation, sequestration, and secretion of drugs through the normal activity of the recycling and secretory compartments. Acidification and efficient functioning of the tubulovesicular compartments comprising the efflux pathway is lost in the drug sensitive cells. As predicted from this hypothesis, agents which disrupt organelle acidification (e.g. monensin, nigericin and amiloride) are effective in reversing the resistance of MDR tumor cells (49, 52, 62). Here we demonstrate that tamoxifen, an anti-estrogen which can reverse adriamycin resistance in vitro and in vivo (49, 63–66), also disrupts the acidification and structure of the exocytotic compartments.

Figure 8:
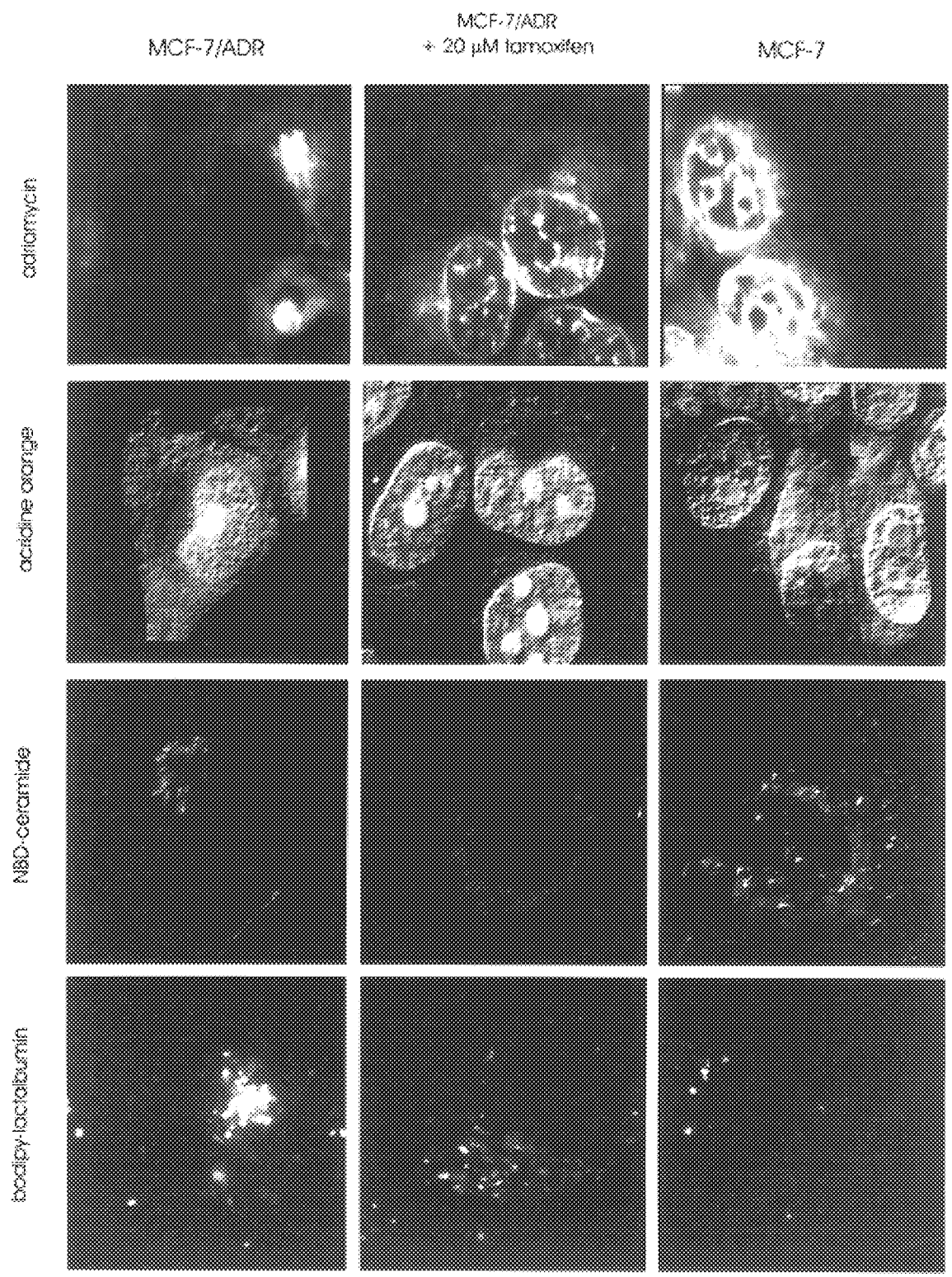
FIG. 8 shows the intracellular redistribution of adriamycin and the disruption of the TGN and PCR in drug resistant human breast cancer cells (MCF-7adr) following treatment with tamoxifen. Cells were seeded and grown in Dulbecco Modified Eagle's media containing 10% fetal calf serum (phenol red free) in Lab-Tek culture chambers (Nunc, Naperville, Ill.) maintained in an incubator at 37° C. and 5% $CO_2$. Human breast cancer cells (MCF-7) and the adriamycin resistant line (MCF-7adr) were obtained from Dr. William W. Wells of the Dept. of Biochemistry, Michigan State U. The media for the MCF-7adr cells was supplemented with adriamycin (0.5 $\mu g$/ml). Cells were utilized 3–4 days following plating. Unless otherwise indicated all cells were labeled at 37C. and then examined at room temperature in optical sections with an Insight Bilateral Laser Scanning Confocal Microscope (Meridian Instruments, Okemos, Mich.).

Tamoxifen changes the intracellular distribution of chemotherapeutics in adriamycin resistant MCF-7 (MCF-7adr) as observed with confocal microscopy. As previously described (62), the majority of adriamycin in MCF-7adr cells is sequestered within tubulovesicular compartments in pericentriolar region of the cell, a minimal level is found in the cytoplasm, and no fluorescence is observed in the nucleoplasm (FIG. 8, top row left). In contrast, in the drug sensitive (MCF-7) cells adriamycin is diffuse through the cell with an accumulation in the nucleus (FIG. 8, top row right). Treatment of MCF-7adr cells with tamoxifen (50M for 15 min.) shifts the adriamycin distribution to that observed in the MCF-7 cells (FIG. 8, top row middle). A similar redistribution of adriamycin to the nucleus was reported following treatment with monensin and verapamil, two modifiers of drug resistance (62).

The pH of intracellular vesicular compartments was examined with acridine orange, a fluorescent reagent that accumulates in acidic compartments and undergoes a shift in fluorescence emission to longer wavelengths as a function of increased concentration (51, 62, 68). MCF-7adr cells show a pericentriolar localization of acridine orange staining, indicative of the uptake of acridine orange into acidic compartments (FIG. 8, 2nd row left) and no acidic compartments are observed in the MCF-7 cells (FIG. 8, 2nd row right) (62). Treatment of the MCF-7adr cells with tamoxifen results in the loss of acridine orange staining within the pericentriolar region (FIG. 8, 2nd row middle) which was also seen following treatment with monensin and verapamil (62). These changes in acidification parallel the redistribution of adriamycin.

The effects of tamoxifen on the structure of the acidic exocytotic compartments was explored with fluorescent probes and confocal microscopy. To examine the structure and organization of the TGN in living cells, the fluorescent probe Bodipy-ceramide was exogenously added to cells in culture. In the Golgi, Bodipy-ceramide is converted to Bodipy-sphingomyelin which then migrates to the TGN. Accumulation of this metabolite in the TGN results in a long wavelength shift in its fluorescence emission (orange in FIG. 8, fourth row) and "red" labeling of the TGN and secretory vesicles. As observed in drug resistant cells (MCF-7-adr), the "red" TGN forms a crescent shaped structure within the pericentriolar region of the nucleus (FIG. 8, fourth row, left). This has been observed for Bodipy-ceramide labeling in a variety of cell types (55). Drug sensitive MCF-7 cells show a pronounced disorganization of the TGN (FIG. 8, fourth row right) with an increase in tubulo-vesicular structures. These structures may represent defective formation or tethered secretory vesicles (62). A similarly disorganized TGN architecture has been observed in cells during mitosis and in cells treated with okadaic acid (69, 70). In all instances, a disrupted TGN architecture is shown to result in either no or defective secretion (69, 70). Treatment of the MCF-7adr cells with tamoxifen produces a similar fragmentation of TGN structure (FIG. 8, fourth row, middle).

Labeling of MCF-7 adr cells with bodipy-lactalbumin, a marker for the intracellular compartments involved in fluid phase endocytosis shows uptake of the dye-protein complex and localization within endosomes and elements of the pericentriolar recycling compartment (PRC) (FIG. 8, third row). Such localization was previously reported for other probes of the recycling pathway in a variety of cells (71, 72). In contrast, MCF-7 cells show only a very diffuse labeling with bodipy-lactalbumin (FIG. 8, 3rd row right). Treatment of MCF-7adr cells with tamoxifen disrupts the structure of the PRC to resemble the labeling in the MCF-7 cells (FIG. 8, 3rd row middle). Similar aberrant organization for the PRC has been described for endocytosis mutants (73).

To examine the effect of tamoxifen on cytotoxicity, cell viability measurements were performed as described in FIG. 9. The addition of tamoxifen to MCF-7adr cells resulted in a significantly enhanced sensitivity to adriamycin.

We propose that an acidic pH within exocytotic compartments results in the protonation, sequestration and concentration of the drug within these vesicles. Rapid secretion of drug is then achieved through the normal activity of the recycling/secretory pathway. Abnormal alkalization of these acidic exocytotic compartments in adriamycin sensitive cells results in the accumulation of drug within the nucleus and cytoplasm leading to cytotoxicity. The ability of tamoxifen to block, or reverse, acidification of these organelles provides an effective means to inhibit drug accumulation within exocytotic compartments and in this manner increase cytosolic and nucleoplasmic concentration of cytotoxic drugs. Tamoxifen has been demonstrated to block ATP-dependent chloride channels (74, 75) and $Cl^-$ is an important counterion for allowing the establishment of proton gradients across the membranes of endosomal and secretory vesicles. The observation that the multi-drug resistance protein Pgp is heavily localized within the Golgi in MCF- 7adr cells (59, 60) suggest that it may be responsible for the "ionic rehabilitation" of the secretory compartments in MCF-7 cells and the resultant drug resistance phenotype.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

The following is a listing of certain of the publications referred to numerically or in abbreviated fashion in the foregoing specification.

1. Ma, L. & Center, M. S. (1992) *Biochem. Biophys. Res. Commun.* 182, 675–681.
2. Cole, S. P. C., Bhardwaj, G., Gerlach, J. H., Mackie, J. E., Grant, C. E., Almquist, K. C., Stewart, A. J., Kurz, E. U., Duncan, A. M. V. & Deeley, R. G. (1992) *Science* 258, 1650–1654.
3. Gottesman, M. M. & Pastan, I. (1993) *Annu. Rev. Biochem.* 62, 385–427.
4. Dano, K. (1973) *Biochim. Biophys. Acta* 323, 466–483.
5. Higgins, C. F. & Gottesman, M. M. (1992) *TIBS* 17, 18–21.
6. Di Marco, A., Casazza, A. M., Dasdia, T., Necco, A., Pratesi, G., Rivolta, P., Velcich, A., Zaccara, A. & Zunino, F. (1977) *Chem. Biol. Interact.* 19, 291–302.
7. Owellen, R. J., Donigian, D. W., Hartke, C. A. & Hains, F. O. (1977) *Biochem. Pharm.* 26, 1213–1219.
8. Skovsgaard, T. (1977) *Biochem. Pharm.* 26, 215–222.
9. Warburg, 0. (1956) *Science* 123, 309–314.
10. Thiebaut, F., Currier, S. J., Whitaker, J., Haugland, R. P., Gottesman, M. M., Pastan, I. & Willinghan, M. C. (1990) *J. Histochem. Cytochem.* 38, 685–690.
11. Zunino, F., Di Marco, A. & Zaccara, A. (1979) *Chem. Biol. Interact.* 24, 217–225.
12. Zunino, F., Gambetta, R., Di Marco, A., Velcich, A., Zaccara, A., Quadrifoglio, F. & Crescenzi, V. (1977) *Biochim. Biophys. Acta* 476, 38–46.
13. Zunino, F., Gambetta, R., Di Marco, A. & Zaccara, A. (1972) *Biochim. Biophys. Acta* 277, 489–498.
14. Di Marco, A., Silvestrini, R., Di Marco, S. & Dasdia, T. (1965) *J. Cell Biol.* 27, 545–550.
15. Calendi, E., Di Marco, A., Reggiani, M., Scarpinato, B. & Valentini, L. (1965) *Biochim. Biophys. Acta* 103, 25–49.
16. Doskocil, J. & Fric, I. (1973) *FEBS Letters* 37, 55–58.
17. Weisenberg, R. C. & Timasheff, S. N. (1970) *Biochemistry* 9, 4110–4116.
18. Na, C. & Timasheff, S. N. (1977) *Archives of Biochemistry and Biophysics* 182, 147–154.
19. Weaver, J. L., Pine, P. S., Aszalos, A., Schoenlein, P. V., Currier, S. J., Padmanabhan, R. & Gottesman, M. M. (1991) *Exp. Cell Res.* 196, 323–329.
20. Boron, W. F. (1986) *Annu. Rev. Physiol.* 48, 377–388.
21. Lin, P., Ahluwalia, M. & Gruenstein, E. (1990) *Am. J. Physiol.* 258, C132–C139.
22. Gillies, R. J., Martinez-Zaguilan, R., Martinez, G. M., Serrano, R. & Perona, R. (1990) *Proc. Natl. Acad. Sci. USA* 87, 7414–7418.
23. Dalmark, M. & Storm, H. H. (1981) *The Journal of General Physiology* 78, 349–364.
24. Mayer, L. D., Bally, M. B. & Cullis, P. R. (1986) *Biochim. Biophys. Acta* 857, 123–126.
25. Keizer, H. G. & Joenje, H. (1989) *J. Natl. Cancer Inst.* 81, 706–709.
26. Nygren, P., Larsson, R., Gruber, A., Peterson, C. & Bergh, J. (1991) *Br. J. Cancer* 64, 1011–1018.
27. Gruber, A., Briese, B., Areström, I., Vitols, S., Björkholm, M. & Peterson, C. (1993) *Leuk. Res.* 17, 353–358.
28. Ling, V. & Thompson, L. H. (1974) *J. Cell. Physiol.* 83, 103–116.
29. Skovsgaard, T. (1978) *Cancer Res.* 38, 1785–1791.
30. Marsh, W., Sicheri, D. & Center, M. S. (1986) *Canc. Res.* 46, 4053–4057.
31. Inaba, M. & Sakurai, Y. (1979) *Cancer Lett.* 8, 111–115.
32. Ramu, A., Pollard, H. B. & Rosario, L. M. (1989) *Int. J. Cancer* 44, 539–547.
33. Sirotnak, F. M., Yang, C. -H., Mines, L. S., Oribé, E. & Biedler, J. L. (1986) *J. Cell. Physiol.* 126, 266–274.
34. Fojo, A., Akiyama, S., Gottesman, M. M. & Pastan, I. (1985) *Cancer Res.* 45, 3002–3007.
35. Carlsen, S. A., Till, J. E. & Ling, V. (1976) *Biochim. Biophys. Acta* 455, 900–912.
36. Beck, W. T., Cirtain, M. C. & Lefko, J. L. (1983) *Mol. Pharmacol.* 24, 485–492.
37. Epand, R. F., Epand, R. M., Gupta, R. S. & Cragoe, E. J.,Jr. (1991) *Br. J. Cancer* 63, 247–251.
38. Mukhopadhyay, K., Parrack, P. K. & Bhattacharyya, B. (1990) *Biochemistry* 29, 6845–6850.
39. Wilson, L. (1970) *Biochemistry* 9, 4999–5007.
40. Beck, W. T. (1987) *Biochem. Pharm.* 36, 2879–2887.
41. Sehested, M., Skovsgaard, T., van Deurs, B. & Winther-Nielsen, H. (1987) *J. Natl. Cancer Inst.* 78, 171–179.
42. Sehested, M., Skovsgaard, T., van Deurs, B. & Winther-Nielsen, H. (1987) *Br. J. Cancer* 56, 747–751.
43. van Adelsberg, J. & Al-Awqati, Q. (1986) *J. Cell Biol.* 102, 1638–1645.
44. Hager, A., Debus, G., Edel, H. -G., Stransky, H. & Serrano, R. (1991) *Planta* 185, 527–537.
45. Mellman, I., Fuchs, R. & Helenius, A.,*Ann. Rev. Biochem,* 55, 663–700 (1986).
46. Maxfield, F. R. & Yasmashiro, D. J. in *Intracellular trafficking of proteins* (eds Steer, C. J. & Hanover, J. A.) 157–182 (Cambridge University Press, Cambridge, 1991).
47. vanDeurs, B., Petersen, O. W., Olsnes, S. & Sandvig, K. *International Review of Cytology,* 117, 131–177 (1989).
48. Tartakoff, A. M. *Cell* 32, 1026–1028 (1983).
49. Simon, S. M. & Schindler, M. *Proc. Natl. Acad. Sci USA* 91, 3497–3504 (1994).
50. Whitaker, J. E., Haugland, R. P. & Prendergast, F. G. *Analytical Biochemistry* 194, 330–344 (1991).
51. Barasch, J., Kiss, B. Prince, A., Saiman, L., Gruenert, D. & Al-Awqati, Q. *Nature (London)* 352, 70–73 (1991).
52. Simon, S. M., Roy, D. & Schindler, M. *Proc. Natl. Acad. Sci. USA* 91, 1128–1132 (1994).
53. Van Dyke, R. & Belcher, J. D. Am. *J. Physiol. Cell Physiol.* 266, C81–C94 (1994).
54. Russell, J. T. & Holz, R. W. *J. Biol. Chem.* 256, 5950–5953 (1981).
55. Pagano, R. E., Martin, O. C., Kang, H. C. & Haughland, R. P. *Journal of Cell Biology* 113, 1267–1279 (1991).
56. Lippincott-Schwartz, J., Yuan, L. C., Tipper, C. Amherdt, M. Orci, L. & Klausner, R. D. *Cell* 67 601–616 (1991).
57. Al-Awqati, Q., Barasch, J. & Landry, D. *J. Exp. Biol.* 172 245–266 (1992).
58. Valverde, M. A., Diaz, M. Speulveda, F. V., Gill, D. R. Hyde, S. C. & Higgins, C. F. *Nature* (London) 355, 830–833 (1992).
59. Willingham, M. C., Richert, N. D., Corwell, M. M. et al. *J. Histochem. Cytochem* 35, 1451–1456 (1987).

60. Molinari, A., Cianfriglia, M., Meschini, S., Calcabrini, A. & Arancia, G. *Int. J. Cancer* 59, 789–795 (1994).
61. Labarca, C. & Paigne, K. *Analytical Biochemistry* 102, 344–352 (1980).
62. Schindler, M. et al *J. Biol. Chem.*, manuscript submitted.
63. Berman, E. et al *Blood* 77, 818 (1991).
64. Chatterjee, M. et al *British J. Cancer* 62, 712 (1990).
65. Hamilto, G. et al *Anticancer Res.* 13, 2059 (1993).
66. Kirk, J. et al *Biochem. Pharmacol.* 48, 277 (1994).
67. Trump, D. L. et al *J. Natl. Canc. Inst.* 84, 1811 (1992).
68. Barasch, J. et al *Nature* 352, 70 (1991).
69. Lucocq, J. *J. Cell Sci.* 103, 875 (1992).
70. Horn, M. and Banting, G. *Biochem. J.* 301, 69 (1994).
71. Koval, M. and Pagano, R. E. *J. Cell Biol.* 108, 2169 (1989).
72. Mayor, S. et al *J. Cell Biol.* 121, 1257 (1993).
73. McGraw, T. E. et al *J. Cell Physiol.* 155, 579 (1993).
74. Zhang, J. J. et al *J. Clin. Invest.* 94, 1690 (1994).
75. Ehring, G. R. et al *J. Gen. Physiol.* 104, 1129 (1994).

What is claimed is:

1. A method for measuring the development or onset of pH-dependent multidrug resistance in a tumor cell in which such multidrug resistance is suspected, comprising determining whether there is a defect in the pH regulatory mechanism of an intracellular vesicular compartment of the cell; wherein said defect is symptomatic of the tumor cell being drug-sensitive; and wherein the absence of said defect is indicative of the onset or development of multidrug resistance in the tumor cell.

2. The method of claim 1 wherein determining whether there is a defect in the pH regulatory mechanism of the intracellular vesicular compartment is performed by determining whether a pH gradient is present between the intracellular vesicular compartment and the cytoplasm of the tumor cell; wherein the absence of the pH gradient is indicative of said defect.

3. The method of claim 2 wherein the tumor cell is infiltrated with a pH indicator prior to determining whether the pH gradient is present.

4. The method of claim 3 wherein the pH indicator is selected from the group consisting of acridine orange and SNAFL-calcein.

5. The method of claim 3 wherein the pH indicator is capable of being measured spectrofluorometrically.

6. The method of claim 5 wherein the pH indicator is capable of measurement by fluorescence microscopy.

7. The method of claim 5 wherein the pH indicator is capable of measurement by confocal microscopy.

8. A method for screening potential drugs to identify candidate drugs for treating pH-dependent multidrug resistance in mammals comprising:

(a) contacting a mammalian tumor cell with a potential drug, wherein the tumor cell is multidrug resistant, and wherein it is determined that a pH gradient is present between the intracellular vesicular compartment and the cytoplasm of the tumor cell prior to said contacting; and (b) determining whether the pH gradient is present in the tumor cell; wherein the absence of the pH gradient identifies the potential drug as a candidate drug for the treatment of multidrug resistance.

9. The method of claim 8 further comprising:

(c) contacting a mammalian non-tumorous cell with the candidate drug, wherein it is determined that a pH gradient is present between the intracellular vesicular compartment and the cytoplasm in the non-tumorous cell prior to said contacting; and (d) determining whether the pH gradient is present in the non-tumorous cell; wherein the presence of the pH gradient in the non-tumorous cell confirms the identification of the candidate drug.

10. The method of claim 8 wherein the tumor cell is selected from the group of cells consisting of a myeloma cell and a fibroblast.

11. The method of claim 8 wherein the tumor cell is infiltrated with a pH indicator.

12. The method of claim 8 wherein a plurality of potential drugs are tested at a plurality of drug concentrations.

13. An assay system for screening a potential drug for the treatment of pH-dependent multidrug resistance (MDR) in mammals comprising a mammalian tumor cell susceptible to or experiencing MDR, a pH indicator, and a means for determining whether there is a defect in the pH regulatory mechanism of an intracellular vesicular compartment of the mammalian tumor cell.

14. A method for treating pH-dependent multidrug resistance in a mammalian tumor cell comprising administering to the tumor cell a pH modulator in an amount effective for disrupting a secretary pathway in the tumor cell and thereby alleviate the multidrug resistance in the tumor cell.

15. The method of claim 14 wherein the pH modulator is administered in association with the administration of a chemotherapeutic agent already under administration to the tumor cell.

16. The method of claim 14 wherein said pH modulator is administered simultaneously with said chemotherapeutic agent.

17. The method of claim 14 wherein the pH modulator is administered in a pharmaceutical composition comprising the pH modulator and said chemotherapeutic agent.

18. The method of claim 14 wherein the pH modulator is administered parenterally.

19. The method of claim 14 wherein the pH modulator is administered orally.

20. A therapeutic composition for the treatment of multidrug resistance in a mammal comprising, in unit dose form, a modulator of cellular pH and a pharmaceutically acceptable excipient.

21. The composition of claim 20 wherein the composition includes a chemotherapeutic agent to which the mammal has developed said multidrug resistance.

* * * * *